United States Patent
Reshetnyak et al.

(10) Patent No.: US 10,512,606 B2
(45) Date of Patent: *Dec. 24, 2019

(54) LIPOSOME STRUCTURES AND METHODS OF USE THEREOF

(71) Applicants: Rhode Island Council on Postsecondary Education, Warwick, RI (US); Yale University, New Haven, CT (US)

(72) Inventors: Yana K. Reshetnyak, South Kingstown, RI (US); Oleg A. Andreev, South Kingstown, RI (US); Donald M. Engelman, New Haven, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 15/691,130

(22) Filed: Aug. 30, 2017

(65) Prior Publication Data

US 2018/0064648 A1  Mar. 8, 2018

Related U.S. Application Data

(63) Continuation of application No. 14/499,600, filed on Sep. 29, 2014, now Pat. No. 9,750,693, which is a continuation of application No. 13/208,902, filed on Aug. 12, 2011, now Pat. No. 8,846,081.

(60) Provisional application No. 61/373,660, filed on Aug. 13, 2010.

(51) Int. Cl.

| | | |
|---|---|---|
| A61K 9/127 | (2006.01) |
| A61K 31/713 | (2006.01) |
| A61K 31/711 | (2006.01) |
| A61K 31/704 | (2006.01) |
| A61K 47/69 | (2017.01) |
| A61K 31/20 | (2006.01) |
| A61K 31/337 | (2006.01) |
| A61K 31/7105 | (2006.01) |
| A61P 35/00 | (2006.01) |

(52) U.S. Cl.
CPC ........... *A61K 9/1271* (2013.01); *A61K 9/127* (2013.01); *A61K 31/20* (2013.01); *A61K 31/337* (2013.01); *A61K 31/704* (2013.01); *A61K 31/711* (2013.01); *A61K 31/713* (2013.01); *A61K 31/7105* (2013.01); *A61K 47/6911* (2017.08); *A61P 35/00* (2018.01)

(58) Field of Classification Search
None
See application file for complete search history.

(56) References Cited

U.S. PATENT DOCUMENTS

| | | |
|---|---|---|
| 5,739,273 A | 4/1998 | Engelman et al. |
| 8,076,451 B2 | 12/2011 | Reshetnyak et al. |
| 8,084,610 B2 | 12/2011 | Summerton |
| 8,846,081 B2 * | 9/2014 | Reshetnyak .......... A61K 9/127 424/450 |
| 9,289,508 B2 | 3/2016 | Reshetnyak et al. |
| 9,750,693 B2 * | 9/2017 | Reshetnyak .......... A61K 9/127 |
| 2005/0025820 A1 | 2/2005 | Kester et al. |
| 2005/0163832 A1 | 7/2005 | Torchilin et al. |
| 2007/0231256 A1 | 10/2007 | Summerton |
| 2008/0124274 A1 | 5/2008 | Summerton |
| 2008/0233107 A1 | 9/2008 | Reshetnyak et al. |
| 2009/0252785 A1 | 10/2009 | Pollock et al. |
| 2010/0150928 A1 | 6/2010 | Ashkenazi et al. |
| 2012/0142042 A1 | 6/2012 | Reshetnyak et al. |

FOREIGN PATENT DOCUMENTS

| | | |
|---|---|---|
| WO | WO-2006078816 A2 | 7/2006 |
| WO | WO-2009073193 A2 | 6/2009 |
| WO | WO-2012047354 A2 | 4/2012 |

OTHER PUBLICATIONS

An et al., pH-(low)-insertion-peptide (pHLIP) translocation of membrane impermeable phalloidin toxin inhibits cancer cell proliferation. Proc Natl Acad Sci U S A. Nov. 23, 2010;107(47):20246-50.
Andreev et al., Mechanism and uses of a membrane peptide that targets tumors and other acidic tissues in vivo. Proc Natl Acad Sci U S A. May 8, 2007;104(19):7893-8.
Antosh et al., "Enhancement of radiation effect on cancer cells by gold-pHLIP", PNAS 2015, doi: 10.1073/pnas.1501628112.
Arachchige et al., "Advanced targeted nanomedicine", 2015, Journal of Biotechnology 202 (2015) 88-97.
Bechara et al., Cell-penetrating peptides: 20 years later, where do we stand? FEBS Lett. Jun. 19, 2013;587(12):1693-702.
Daniels et al., "Synthesis and Characterization of pHLIP Coated Gold Nanoparticles", Biochemistry and Biophysics Reports vol. 10, 2017, pp. 62-69.
Hendrickson et al., Incorporation of nonnatural amino acids into proteins. Annu Rev Biochem. 2004;73:147-76.
Mata et al., Tumor imaging using technetium-99m bound to pH-sensitive peptides. Nanomedicine. 2007;3(4):297-305.
Musial-Siwek et al., Tuning the insertion properties of pHLIP. Biochim Biophys Acta. Jun. 2010;1798(6):1041-6.
Pereira et al. "pH-sentitive pHLIP Coated Niosomes", Mol Membr Biol. 2016; 33(3-5): 51-63.
Reshetnyak et al. "A Monomeric Membrane Peptide That Lives in Three Worlds: In Solution, Attached to, and Inserted Across Lipid Bilayers." Biophys. J. 2007;93:2363-2372.
Sosunov et al. pH (low) insertion peptide (pHLIP) targets ischemic myocardium, PNAS Jan. 2, 2013. 110 (1) 82-86.
Thevenin et al. pHLIP-Mediated Translocation of Membrane-Impermeable Molecules into Cells. Chem. Biol. 2009;16:754-762.
Vanniasinghe et al., The potential of liposomal drug delivery for the treatment of inflammatory arthritis. Semin Arthritis Rheum. 2009;39(3):182-96.

(Continued)

*Primary Examiner* — James D Schultz
(74) *Attorney, Agent, or Firm* — Mintz Levin Cohn Ferris Glovsky and Popeo, P.C.; Ingrid A. Beattie

(57) ABSTRACT

The present application relates to compositions comprising and methods of using a liposome comprising a pHLIP polypeptide, wherein a lipid bilayer of the liposome is substantially free of the pHLIP polypeptide.

24 Claims, 33 Drawing Sheets

Specification includes a Sequence Listing.

(56) References Cited

OTHER PUBLICATIONS

Andreev, Oleg A., et al. "pH (low) insertion peptide (pHLIP) inserts across a lipid bilayer as a helix and exits by a different path." Proceedings of the National Academy of Sciences 107.9 (2010): 4081-4086.
Andreev, Oleg A., Donald M. Engelman, and Yana K Reshetnyak. "Targeting acidic diseased tissue: New technology based on use of the pH (Low) Insertion Peptide (pHLIP)." Chimica oggi 27.2 (2009): 34-37.
Reshetnyak, Yana K., et al. "Energetics of peptide (pHLIP) binding to and folding across a lipid bilayer membrane." Proceedings of the National Academy of Sciences 105.40 (2008): 15340-15345.
Reshetnyak, Yana K., et al. "Translocation of molecules into cells by pH-dependent insertion of a transmembrane helix." Proceedings of the National Academy of Sciences 103.17 (2006): 6460-6465.
Segala, James, et al. "Accurate analysis of tumor margins using a fluorescent pH low insertion peptide (pHLIP)." International journal of molecular sciences 10.8 (2009): 3478-3487.
Vavere, Amy L., et al. "A novel technology for the imaging of acidic prostate tumors by positron emission tomography." Cancer research 69.10 (2009): 4510-4516.
Wijesinghe, Dayanjali, et al. "pH dependent transfer of nano-pores into membrane of cancer cells to induce apoptosis." Scientific reports 3 (2013): 3560 (1-7).
Zoonens, Manuela, Yana K. Reshetnyak, and Donald M. Engelman. "Bilayer interactions of pHLIP, a peptide that can deliver drugs and target tumors." Biophysical journal 95.1 (2008): 225-235.

* cited by examiner

Figure 2A1.
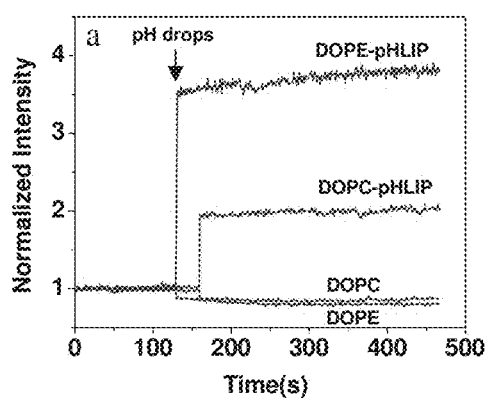
Figure 2A2.
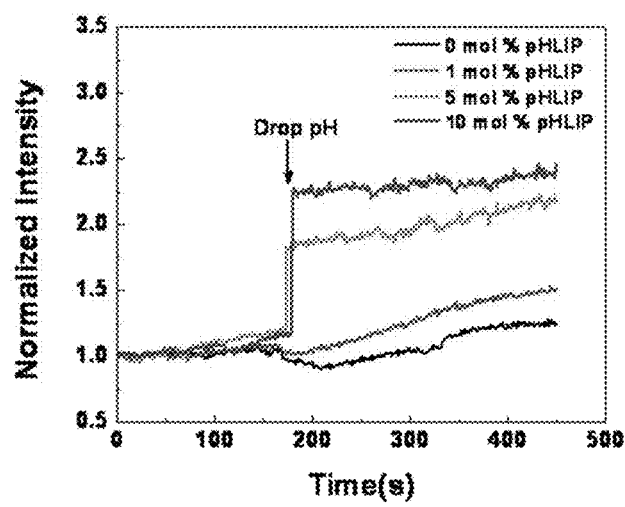

DOPE

DOPE-pHLIP

DOPC

DOPC-pHLIP

Seed A549 cells into 96-well plate
(10k cells / well)

overnight 1 hour treatment with liposome
(various concentration) in pH 6
and pH 8 phosphate buffer Refresh medium Run MTS assay
after overnight incubation A549 cells in suspension (1mL,160k )

Spin down and remove supernatant

Wash once with 1mL DMEM

Reseed cells into 96-well plate
(5000 cells / well)

Run MTS assay
after 3 or 4 days incubation

LIPOSOME STRUCTURES AND METHODS OF USE THEREOF

RELATED APPLICATIONS

This application is a continuation of U.S. application Ser. No. 14/499,600, filed Sep. 29, 2014, which is a continuation of U.S. application Ser. No. 13/208,902, filed Aug. 12, 2011, now U.S. Pat. No. 8,846,081, issued Sep. 30, 2014, which claims the benefit of priority under 35 U.S.C. § 119(e) to U.S. Provisional Application No. 61/373,660, filed Aug. 13, 2010, which are incorporated herein by reference in their entireties.

STATEMENT AS TO FEDERALLY SPONSORED RESEARCH

This invention was made with U.S. Government support under Grant Number W81XWH-07-1-0498 awarded by the ARMY/MRMC as well as Grand Number R01 CA133890 awarded by the National Institutes of Health. The Government has certain rights in the invention.

INCORPORATION-BY-REFERENCE OF SEQUENCE LISTING

The contents of the test file named "40984-503C02US_ST25.txt", which was created on Aug. 30, 2017 and is 20.3 KB in size, are thereby incorporated by reference in their entirety.

FIELD OF THE INVENTION

The invention relates to compositions and methods for delivery of molecules to cells.

BACKGROUND

Despite many advances in the field of cancer diagnosis and treatment, a reliable method of identifying and treating cancer cells while sparing non-cancerous cells has been elusive. One of the limitations is the heterogeneity of human cancers. It has therefore been problematic to rely on any single tumor biomarker even for one type of cancer. Selective and efficient targeting and delivery of therapeutic agents to tumor cells remains a challenge. As such, there is a pressing need to develop new strategies for the introduction of various agents to cells.

SUMMARY OF THE INVENTION

The invention is based on the surprising discovery that pH (Low) Insertion Peptide (pHLIP) liposomes target acidic tissue, and release liposome content, i.e., cargo into a cell. The compositions and methods of the invention provide a liposome comprising a pHLIP polypeptide, wherein a hydrophobic region of the lipid bilayer of the liposome is substantially free of the pHLIP polypeptide. pHLIP is directly attached to the polar headgroup of the phospholipid or is attached to a polymer (PEG), which in turn is attached to the polar headgroup, but it does not span the hydrophobic phospholipid tail region of the pHLIP-liposome. Optionally, pHLIP can be attached directly to the lipid bilayer.

In some cases, the pHLIP polypeptide is conjugated to a pharmaceutically acceptable polymer (e.g., polymer of polyethylene glycol (PEG), tetrafunctional polyethylene oxide (PEO), polypropylene oxide (PPO), or ethylenediamine block copolymer). For example, the pHLIP polypeptide is attached to polymer-phospholipid (e.g., PEG-phospholipid). The polymer-phospholipid is attached to a terminal end of the pHLIP polypeptide. The PEG serves a dual purpose of protecting the liposome against immune destruction (e.g., uptake and clearance by macrophages) and holding the pHLIP away from the lipid bilayer of the liposome. Optionally, the amino-terminal end of the pHLIP is attached to the PEG portion of the PEG-phospholipid, and the carboxy-terminal end of the pHLIP is located outside of liposome's lipid bilayer, i.e., the pHLIP does not span the lipid bilayer area of the liposome. Alternatively, a reversible peptide such as pHLIP reverse sequence, TEDADVLLALDLLLLPT-TFLWDAYRAWYPNQECA (SEQ ID NO: 41), is used. In that case, the carboxy-terminal end of the pHLIP is attached to the PEG portion of the PEG-phospholipid, and the amino-terminal end of the pHLIP is located outside the liposome's lipid bilayer. In another example, pHLIP is attached directly to a phospholipid in the lipid bilayer. In either example, pHLIP decorates the outside of the liposome.

In some embodiments, the liposome further comprises a cargo inside of the liposome or inside of the lipid bilayer. pHLIP liposomes target diseased tissue in a pH-dependent manner and release liposome content, i.e., cargo into diseased cells. The cargo may comprise any molecule. For example, the cargo comprises a therapeutic compound, such as a polar composition or a non-polar composition. Polar cargo is encapsulated within the liposome, while non-polar cargo is contained in the lipid bilayer of the liposome. Polar cargo molecules include a polar toxin, a small interfering ribonucleic acid (siRNA), a deoxyribonucleic acid (DNA), a phallotoxin, or a polar inhibitor. Non-polar molecules including non-polar inhibitors are also suitable for the methods described herein.

The liposome may further comprise a lipid bilayer-tethered cargo. The tethered cargo is attached to a lipid by a cleavable or non-cleavable bond. In some embodiments, the tethered cargo is attached to a lipid by a S—S bond. In another embodiment, the liposome further comprises hydrophobic cargo incorporated into the lipid bilayer of the liposome. By a "hydrophobic" molecule is meant a molecule having little or no affinity for water. For example, paclitaxel (Taxol®) is an exemplary hydrophobic cargo.

Other exemplary cargo molecules include a DNA-binding agent, ceramide, doxorubicin, Doxil® (a pegylated (polyethylene glycol coated) liposome-encapsulated form of doxorubicin), and Myocet™ (a non-pegylated liposome-encapsulated for of doxorubicin).

Without pHLIP-liposomes, many polar and hydrophobic agents, e.g., chemotherapeutic/antitumor drugs, are only inefficiently taken up by target cells. For example, very polar molecules include sulfonates and phosphonates.

Polar Surface Area (PSA) is a commonly used medicinal chemistry metric for the optimisation of a drug's ability to permeate cells. Molecules with a polar surface area of greater than 140 angstroms squared tend to be poor at permeating cell membranes. A significant advantage of the invention is that even compounds that in the past have been characterized as being poor at permeating cells are successfully delivered into cells and released inside the cells using pHLIP-liposomes.

A method of delivering a cargo into a target cell is carried out by contacting the target cell with a cargo-loaded pHLIP-decorated (pHLIP$^+$) liposome. Preferably, hydrophobic region of the lipid bilayer of the pHLIP$^+$ liposome is substantially free of pHLIP polypeptide. The use of pHLIP-containing liposomes leads to at least 1%, 5%, 10%, 25%, 50%, or 2-fold, 5-fold, 10-fold or more of cargo delivered to the cytoplasm of the target cell compared to the amount delivered using pHLIP⁻ liposome (i.e., a liposome that does not contain a pHLIP). pHLIP⁺ liposomes deliver their cargo to cells by fusion with the cell membrane, by endocytosis, or both. The target cell may be characterized by a microenvironment comprising a low pH.

In some embodiments, the pHLIP⁺ liposome fuses with a cell membrane of the target cell. In some cases, the pHLIP⁺ liposome both fuses with a cell membrane of the target cell and is taken up by the cell by endocytosis. For example, the pHLIP+ liposome preferentially fuses with a membrane of an endosomal and/or a lysosomal compartment of the target cell after uptake by endocytosis.

For example, the target cell is a tumor cell or other cell characterized by a local microenvironment of low pH, e.g., cells of a diseased tissue with a naturally acidic extracellular environment or cells of a tissue with an artificially induced acidic extracellular environment relative to normal physiological pH. Many diseased tissues are characterized by an acidic microenvironment. However, acidity in tumors or non-tumor target tissues is optionally induced by co-injection of glucose or a diluted solution of acid at the tissue site at which therapy using the compositions is desired. For example, an acidifying composition (e.g., glucose or dilute acid) is administered, e.g., injected subcutaneously, before delivery of the pH sensitive compositions (30 s, 1 min., 5 min., 10 min., 30 min., 1 hr., 2 hrs, 6 hrs, 12 hrs, 24 hrs, 48 hrs, or more prior to administration of the environmentally sensitive composition to the target tissue site). Alternatively, the tissue acidifying agent and the pHLIP composition are co-administered. For example, the diseased tissue is selected from the group consisting of cancer, inflammation/inflamed tissue, ischemia/ischemic tissue, tissue affected by stroke, arthritis, infection with a microorganism (e.g., a bacteria, virus, or fungus), or atherosclerotic plaques.

pHLIP-liposomes are also useful to deliver therapeutic agents or diagnostic agents to cell surfaces in a diseased tissue with a naturally acidic extracellular environment or in a tissue with an artificially induced acidic extracellular environment relative to normal physiological pH. Administration of a neutralizing agent to an acidic site, e.g., a bicarbonate solution, is used to reduce pHLIP binding/insertion and pHLIP labeling or targeting of cells at that site.

Pharmaceutical compositions comprising the liposomal structures according to the present embodiments are also within the invention pHLIP peptides comprise a membrane sequence that comprises at least 8 amino acids. Preferably, the length of the peptide does not exceed 50 amino acids (excluding the cargo moiety). pHLIP peptides are characterized by pH-dependent membrane-binding or membrane-inserting activity. A membrane sequence is an amino acid sequence of a peptide that associates with or inserts into a lipid bilayer. For example, the membrane sequence of the peptide spans a cell membrane structure. The membrane sequence mediates translocation of a composition (e.g., cargo compounds) that is attached to, e.g., conjugated to, the membrane sequence. Translocation means translocation of cargo across a membrane of an artificial lipid bilayer structure and/or that of a cell. The peptide component of the composition (e.g., membrane sequence) is monomeric and non-pore forming, i.e., a peptide comprising the membrane sequence does not assemble into a multimeric pore or channel structure in a lipid bilayer or cell membrane. For example, insertion of the membrane sequence of the composition into a lipid membrane does not cause calcium release out of lipid vescicles and does not cause hemoglobin leakage out of red blood cells.

The membrane sequence comprises greater than 8 and less than 50 residues. Preferably, the range is 13-25 residues. At least 6 of the 8 amino acids of the insertion sequence are non-polar. In some embodiments, the 6 non-polar amino acids of the membrane sequence are contiguous. At least one of the 8 amino acids of the insertion sequence is protonatable. The protonatable amino acid is located within 10 amino acids (e.g., within 2, 3, 4, 5, 6, 7, 8, or 9 residues) of the non-polar amino acids (not immediately contiguous to a non-polar amino acid). The peptide comprises naturally-occurring amino acids, non-naturally occurring amino acids, amino acids that are DNA-encoded as well as those that are not encoded by DNA or RNA. The peptide includes L-amino acids as well as D-amino acids.

All polynucleotides and polypeptides of the invention are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybridgene, i.e., a gene encoding a fusion protein. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides the nucleic acid molecule, the two phrases can be used interchangeably.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Specifically, PCT/US2011/043928, filed Jul. 13, 2011 is incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 2A1 is a line graph showing pHLIP-induced inter-liposome fusion in low pH solution. pHLIP-mediated inter-liposome fusion was studied by Octadecyl rhodamine B (R18) self-quenching assay. Liposomes labeled with R18 were mixed with various concentrations of unlabeled liposomes (POPC). During the process of dropping pH of solution, rhodamine fluorescence was monitored on the spectrofluorometer. The rhodamine fluorescence of pHLIP-liposomes (DOPE-pHLIP or DOPC-pHLIP) increase significantly after dropping pH.

FIG. 2A2 is a line graph showing pHLIP-induced inter-liposome fusion in low pH solution. pHLIP-mediated inter-liposome fusion was studied by Octadecyl rhodamine B (R18) self-quenching assay. Liposomes labeled with R18 were mixed with various concentrations of unlabeled liposomes (POPC). During the process of dropping pH of solution, rhodamine fluorescence was monitored on the spectrofluorometer. The rhodamine fluorescence of pHLIP-liposomes (DOPE-pHLIP or DOPC-pHLIP) containing various % of pHLIP increase.

FIG. 24B shows that there is increase of fluorescence when pHLIP-coated liposomes are mixed with POPC liposomes, which indicates fusion of liposomes. Thus, pHLIP promotes fusion only at low pH.

DETAILED DESCRIPTION OF THE INVENTION

The invention is based on the discovery that pHLIP-liposomes target the acidic microenvironment of a tissue, and release liposome content, i.e., cargo, into a cell. Because pHLIP does not insert into cellular membranes at normal pH, pHLIP allows for the selective delivery of cargo molecules to diseased tissue with low extracellular pH by preventing the entry of cargo molecules into a healthy cell.

Figure 1:
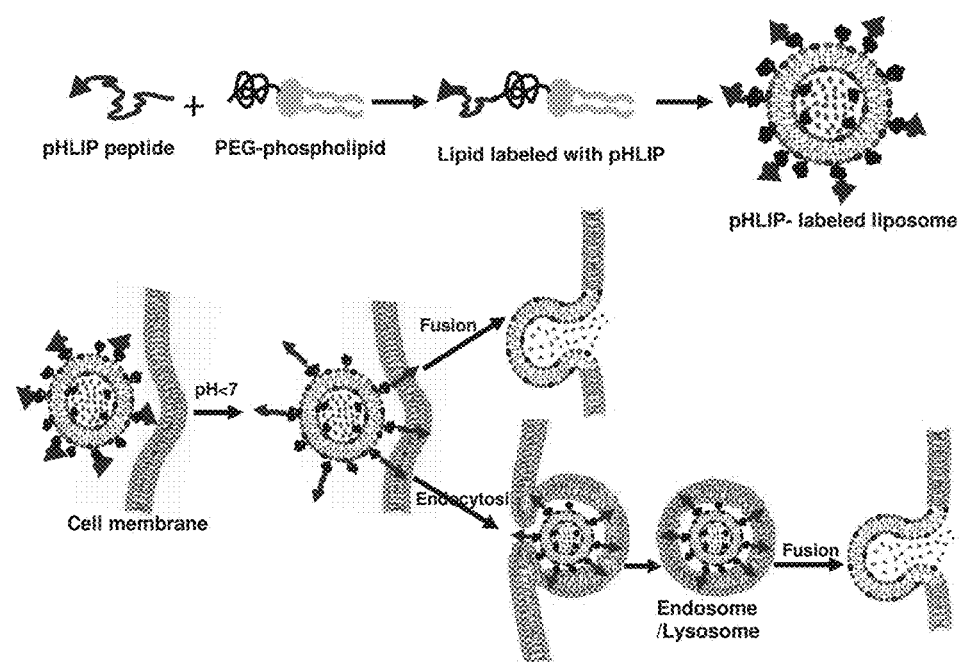
FIG. 1 is a schematic presentation of pHLIP-mediated fusion or endocytotic uptake of liposomes. The triangle represents the carboxy (COOH) end of the pHLIP, which is most distant from the lipid bilayer of the liposome. The amino ($NH_2$) end of pHLIP is attached to the PEG portion of the PEG-phospholipid.

Prior to the invention described herein, the release of liposome content into cells was problematic due to the entrapment of liposomes and their contents within the endosomal compartments after endocytosis. As described herein, pHLIP promotes the fusion of liposomes with cellular membranes or the fusion of liposomes with endosome membranes after endocytotic uptake of pHLIP liposomes, thereby releasing the contents of the liposomes into the cell. These two mechanisms of action are illustrated in FIG. 1.

Figure 29:
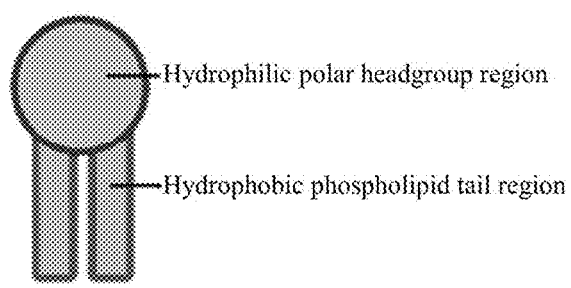
FIG. 29 is a schematic depicting the hydrophilic polar headgroup region and hydrophobic phospholipid tail region of a liposome.

The hydrophobic region of the lipid bilayer of an exemplary pHLIP-liposome is substantially free of the pHLIP polypeptide. pHLIP is directly attached to the polar headgroup of the phospholipid or is attached to a polymer (PEG), which in turn is attached to the polar headgroup, but pHLIP peptide does not span the hydrophobic phospholipid tail region of the pHLIP-liposome. Alternatively or optionally, pHLIP is attached directly to the lipid bilayer. A schematic depicting the hydrophilic polar headgroup region and hydrophobic phospholipid tail region of a liposome is provided in FIG. 29.

In some cases, pHLIP liposomes deliver molecules to the inside of a cell by inserting into a cellular lipid bilayer and transporting C-terminal cargo molecules across the plasma membrane. Any molecule is a suitable cargo molecule. Exemplary functional cargo molecules include peptide nucleic acid (PNA), phalloidin, doxorubicin, and paclitaxel.

Peptide nucleic acid (PNA) is an artificially synthesized polymer similar to DNA or RNA; however, the backbone of PNA is composed of repeating N-(2-aminoethyl)-glycine units linked by peptide bonds. Since the backbone of PNA contains no charged phosphate groups, the binding between PNA and DNA strands is stronger than between DNA/DNA strands due to the lack of electrostatic repulsion. In this manner, PNA acts as a gene regulation agent by exhibiting antisense activity. Although PNA itself has poor membrane permeability, pHLIP liposomes significantly enhance its translocation and antisense activity.

Phalloidin, a cytotoxin isolated from the Death Cap mushroom *Amanita phalloides*, is a polar, cell-impermeable, cyclic heptapeptide (An et al., 2010 PNAS, 107(47): 20246-20250). Because phalloidin is cell-impermeable, prior to the invention described herein, phalloidin was not suitable for therapeutic purposes. As described herein, pHLIP liposomes deliver phalloidin into the cytoplasm of cells, thereby preventing cell migration and metastasis.

Doxorubicin intercalates DNA, and is commonly used in the treatment of a wide range of cancers. Similarly, paclitaxel (Taxol®) is a mitotic inhibitor used in cancer chemotherapy. pHLIP liposomes selectively deliver cancer agents into the cytoplasm of diseased cells with low extracellular pH. In this manner, drug efficacy is enhanced, and the side effects of anti-cancer therapy are reduced.

Numerous pHLIP peptide sequences are described in WO 2006/078816 A2, herein incorporated by reference. The invention is based on the surprising discovery that a liposome comprising a pHLIP peptide is useful for enhanced delivery of agents (particularly agents that are difficult to deliver using other methods) to target cells characterized by a low pH microenvironment, e.g., tumor cells.

As described above, an acidic environment triggers insertion of pHIP into synthetic lipid bilayer structures or cellular membrane in vitro and in vivo. As described herein, since acidity is associated with many pathological states, including cancer, pHLIP is used as a disease-targeting acid-specific peptide. Described herein is the selective delivery of gold nanoparticles and pHLIP liposomes to cancer cells in vivo. Gold nanospheres and nanorods are used for the enhancement of radiation therapy and for thermal ablation of tumors.

A major challenge is to selectively deliver enough gold material to cancer cells to produce the desirable effect. The compositions and methods of the invention overcome the drawbacks and challenges associated with previous methods. The in vivo data described herein shows high uptake of pHLIP-labeled liposomes by cancer cells and efficient delivery of cargo to such cells.

Liposomal Structures

The liposomes of some embodiments comprise polymer-phospholipids (e.g., PEG-phospholipid). In some embodiments, the pHLIP polypeptide is attached to polymer-phospholipid (e.g., PEG-phospholipid). The polymer-phospholipid may be attached at the terminal end of the pHLIP polypeptide. In some embodiments, the amino-terminal end of pHLIP is attached to the PEG-phospholipid and the carboxy-terminal end of pHLIP is located outside of the liposome.

In some embodiments, the bilayer of the liposome comprises at least 1, 2, 5, 8 or 10% polymer (e.g., at least 15%, at least 20%, at least 25%, at least 30%, at least 40%, at least 50%, at least 60%, at least 70%, at least 80%, at least 90%, at least 95%). In some embodiments, the inner lipid bilayer contains less than 40% of total polymer (less than 30%, 25%, 20%, 15%, 10%, or 5%). In some embodiments, the outer lipid bilayer contains at least 60% of total polymer (more than 60%, 65%, 70%, 75%, 80%, 90%, or 95%) contained in the liposome.

In some embodiments, the bilayer of the liposome comprises at least 10% PEG (e.g., at least 15%, at least 20%, at least 25%, at least 30%, at least 40%, at least 50%, at least 60%, at least 70%, at least 80%, at least 90%, at least 95%). In some embodiments, the inner lipid bilayer contains less than 40% of total PEG (less than 30%, 25%, 20%, 15%, 10%, or 5%). In some embodiments, the outer lipid bilayer contains at least 60% of total PEG (more than 60%, 65%, 70%, 75%, 80%, 90%, or 95%) contained in the liposome. The PEG may have a molecular weight of MW about 350, 550, 750, 1000, 2000, 5000, or 10000.

pHLIP promotes the following activities: endocytotic uptake of liposomes with up to 10 mol % of PEG polymer (5 mol % is on the surface of liposome in the other leaflet) at low pH; disruption of endosome and lysozome and release of lipids from liposome and liposomal content into cytoplasm; fusion between cell membranes and lipid bilayer of liposome at low pH; delivery of R18 (Rhodamine-fatty acid) to mitochondria in low pH extracellular environment; release of DNA-targeting dye PI (propidium iodide) encapsulated into liposome; delivery of gold nanoparticles to internal cellular membranes at low pH. R18 has affinity to mitochondria membrane, but when delivered by regular liposomes it could not reach mitochondria. Using pHLIP-liposomes, such compounds, and in fact, any mitochondria-targeting compound are readily delivered to intracellular organelles such as mitochondria. In another example, pH-dependent delivery of any polar compounds, e.g., polar agents used for imaging or therapy suitable for encapsulation in liposomes, and any non-polar molecules optionally trapped within lipids of liposome is enhanced using pHLIP-liposomes compared to conventional liposomes (i.e., liposomes that do not contain pHLIP).

pHLIP Sequences

Tables 1-2 provide a summary of exemplary pHLIP sequences used in pHLIP-liposomes. Table 1 includes long pHLIP sequences. The sequences of Table 1, if they insert into a membrane, go across with their C-terminus and leave N-terminus in the extracellular space.

TABLE 1

| Name | Sequence | |
|---|---|---|
| WT-1a | GEQNPIYWARYADWLFTTPLLLLDLALLVDADEG | SEQ ID NO: 1 |
| WT-1b | ACEQNPIYWARYWARYADWLFTTPLLLLDLALLVDADEGTS | SEQ ID NO: 2 |
| WT-1 | GGEQNPIYWARYADWLFTTPLLLLDLALLVDADEGT | SEQ ID NO: 3 |
| WT-2 | ACEQNPIYWARYADWLFTTPLLLLDLALLVDADET | SEQ ID NO: 4 |
| WT-Cys1 | AAEQNPIYWARYADWLFTTPLLLLDLALLVDADEGTCG | SEQ ID NO: 5 |
| WT-Cys2 | AEQNPIYWARYADWLFTTPLLLLDLALLVDADEGCT | SEQ ID NO: 52 |
| WT-Cys3 | GGEQNPIYWARYADWLFTTPLLLLDLALLVDADEGTCG | SEQ ID NO: 6 |
| Cys-WT1 | ACEQNPIYWARYADWLFTTPLLLLDLALLVDADEGTG | SEQ ID NO: 7 |
| Cys-WT2 | ACEQNPIYWARYADWLFTTPLLLLDLALLVDADEGT | SEQ ID NO: 8 |
| Lys-WT | AKEQNPIYWARYADWLFTTPLLLLDLALLVDADEGT | SEQ ID NO: 9 |
| WT-KC | AAEQNPIYWARYADWLFTTPLLLLDLALLVDADEGTKCG | SEQ ID NO: 10 |
| K-WT-C | AKEQNPIYWARYADWLFTTPLLLLDLALLVDADECT | SEQ ID NO: 11 |
| N-pHLIP | ACEQNPIYWARYANWLFTTPLLLLNLALLVDADEGTG | SEQ ID NO: 12 |
| K-pHLIP | ACEQNPIYWARYAKWLFTTPLLLLKLALLVDADEGTG | SEQ ID NO: 13 |
| NNQ | GGEQNPIYWARYADWLFTTPLLLLDLALLVNANQGT | SEQ ID NO: 14 |
| D25A | AAEQNPIYWARYADWLFTTPLLLLALALLVDADEGT | SEQ ID NO: 15 |
| D14A | AAEQNPIYWARYAAWLFTTPLLLLDLALLVDADEGT | SEQ ID NO: 16 |
| P20A | AAEQNPIYWARYADWLFTTALLLLDLALLVDADEGT | SEQ ID NO: 17 |
| D25E | AAEQNPIYWARYADWLFTTPLLLLELALLVDADEGT | SEQ ID NO: 18 |
| D14E | AAEQNPIYWARYAEWLFTTPLLLLDLALLVDADEGT | SEQ ID NO: 19 |
| 3D | AAEQNPIIYWARYADWLFTDLPLLLLDLLALLVDADEGT | SEQ ID NO: 20 |
| R11Q | GEQNPIYWAQYADWLFTTPLLLLDLALLVDADEGTCG | SEQ ID NO: 21 |
| D25Up | GGEQNPIYWARYADWLFTTPLLLDLLALLVDADEGTCG | SEQ ID NO: 22 |
| D25Down | GGEQNPIYWARYADWLFTTPLLLLLDALLVDADEGTCG | SEQ ID NO: 23 |
| D14Up | GGEQNPIYWARYDAWLFTTPLLLLDLALLVDADEGTCG | SEQ ID NO: 24 |
| D14Down | GGEQNPIYWARYAWDLFTTPLILLDLALLVDADEGTCG | SEQ ID NO: 25 |
| P20G | AAEQNPIYWARYADWLFTTGLLLLDLALLVDADEGT | SEQ ID NO: 26 |
| H1 | DDDEDNPIYWARYADWLFTTPLLLLHGALLVDADECT | SEQ ID NO: 27 |
| H2 | DDDEDNPIYWARYAHWLFTTPLLLLHGALLVDADEGCT | SEQ ID NO: 28 |
| H2N | DDDEDNPIYWARYAHWLFTTPLLLLHGALLVNADECT | SEQ ID NO: 29 |
| H2N2 | DDDEDNPIYWARYAHWLFTTPLLLLHGALLVNANECT | SEQ ID NO: 30 |
| 1a-Trp | AEQNPIYWARYADFLFTTPLLLLDLALLVDADET | SEQ ID NO: 31 |
| 1b-Trp | AEQNPIYFARYADWLFTTPLLLLDLALLVDADEGT | SEQ ID NO: 32 |
| 1c-Trp | AEQNPIYFARYADFLFTTPLLLLDLALLWDADET | SEQ ID NO: 33 |
| Fast-1 | AKEDQNPYWARYADWLFTTPLLLLDLALLVDG | SEQ ID NO: 34 |

TABLE 1-continued

| Name | Sequence | |
|---|---|---|
| Cys-Fast1 | AC̲E̲DQNPYWARYADWLFTTPLLLLDLALLVDG | SEQ ID NO: 35 |
| Fast1-Cys | AE̲DQNPYWARYADWLFTTPLLLLDLALLVDC̲G | SEQ ID NO: 36 |
| Fast1-E-Cys | AE̲DQNPYWARYADWLFTTPLLLLE̲LALLVEC̲G | SEQ ID NO: 37 |
| Fast2 | AKE̲DQNPYWR̲AYADLFTPLTLLDLLALWDG | SEQ ID NO: 38 |
| Cys-Fast2 | AC̲E̲DQNPYWR̲AYADLFTPLTLLDLLALWDG | SEQ ID NO: 39 |
| Fastest | AKE̲DQND̲PYWARYADWLFTTPLLLLDLALLVG | SEQ ID NO: 40 |

Table 2 includes sequences termed short and medium pHLIP sequences. They all insert in membrane in a pH-dependent manner, while they do not have C-terminal flanking sequence. Double underline indicates residues (Cys or Lys), which are used to conjugate pHLIPs with cargo molecules. pHLIP sequences contain L-amino acids; alternatively, the pHLIP comprises D-amino acids.

TABLE 2

| Name | Sequence | |
|---|---|---|
| WT-reverse | TEDADVLLALDLLLLPTTFLWDAYRAWYPNQECA | SEQ ID NO: 41 |
| Sh | AEQNPIYW ARYADWLFTTPL | SEQ ID NO: 42 |
| Sh-Cys | AEQNPIYW ARYADWLFTTPC̲L | SEQ ID NO: 43 |
| Cys-Sh | AC̲EQNPIYW ARYADWLFTTPL | SEQ ID NO: 44 |
| Sh-1 Trp | AEQNPIYFARYADWLFTTPL | SEQ ID NO: 45 |
| Sh-1D | K̲EDQNPWARYADLLFPTTLAW | SEQ ID NO: 46 |
| Cys-Sh-1D | AC̲EDQNPWARYADLLFPTTLAW | SEQ ID NO: 47 |
| Cys-Med-2D | AC̲EDQNPWARYADWLFPTTLLLLD | SEQ ID NO: 48 |
| Cys-Sh-1E | AC̲EEQNPWARYAELLFPTTLAW | SEQ ID NO: 49 |
| Cys-Med-2E | AC̲EEQNPWARYAEWLFPTTLLLLE | SEQ ID NO: 50 |
| Cys-Med-3E | AC̲EEQNPWARYLEWLFPTETLLLEL | SEQ ID NO: 51 |

DNA-encoded and non-coded amino acids are described below in Table 3. Additional non-natural amino acids that can be used are known in the art, e.g., as described in Hendrickson et al., 2004, Ann. Rev. Biochem. 73:147-176; hereby incorporated by reference.

TABLE 3

Coded and Non-Coded Amino Acids

| NO: | abbrev | name[s] |
|---|---|---|
| 1 | Ala | alanine |
| 2 | Arg | arginine |
| 3 | Asn | asparagine |
| 4 | Asp | aspartic acid |
| 5 | Cys | cysteine |
| 6 | Gln | glutamine |
| 7 | Glu | glutamic acid |
| 8 | Gly | glycine |
| 9 | His | histidine |
| 10 | Ile | isoleucine |
| 11 | Leu | leucine |
| 12 | Lys | lysine |
| 13 | Met | methionine |
| 14 | Phe | Phenylalanine |
| 15 | Pro | proline |
| 16 | Ser | serine |
| 17 | Thr | threonine |
| 18 | Trp | tryptophan |
| 19 | Tyr | tyrosine |
| 20 | Val | valine |
| 21 | Acpa | Aminocaprylic acid |
| 22 | Aecys | (S)-2-aminoethyl-L-cysteine•HCl |
| 23 | Afa | Aminophenyl acetate |
| 24 | Aiba | -aminoisobytyric acid |
| 25 | Aile | alloisoleucine |
| 26 | Alg | L-allylglycine |
| 27 | Aba | amlnobutyric acid |
| 28 | Aphe | p-aminophenylalanine |
| 29 | Bat | -alanine |
| 30 | Brphe | p-bromophenylalanine |
| 31 | Cha | cyclohexylalanine |
| 32 | Cit | citrulline |
| 33 | Clala | -chloroalanine |
| 34 | Cie | cycioleucine |
| 35 | Clphe | p-chiorophenylalanine |
| 36 | Cya | cysteic acid |
| 37 | Dab | 2,4-diamino-butyric acid |
| 38 | Dap | 2,3-diaminopropionic acid |
| 39 | Dhp | 3,4-dehydro-proline |
| 40 | Dhphe | 3,4-, dihydroxy-phenyl-alanine |
| 41 | Fphe | p-fluorophenylalanine |
| 42 | Gaa | D-glucose-aminic acid |
| 43 | Hag | Homo-arginine |
| 44 | Hlys | hydroxyl-lysine•HCl |
| 45 | Hnvl | DL-hydroxynorvaline |
| 46 | Hog | Homoglutamine |
| 47 | Hoph | homophenylalanlne |
| 48 | Has | homoserine |
| 49 | Hpr | hydroxyl-proline |
| 50 | Iphe | p-Iodophenylalanine |
| 51 | Ise | isoserine |
| 52 | Mle | -methyl-leucine |
| 53 | Msmet | DL-methionine-s-methylsulfo-niumchloride |
| 54 | 1Nala | 3-(1-naphthyl)alanine |
| 55 | 2Nala | 3-(2-naphthyl)alanine |
| 56 | Nle | norleucine (or 2-aminohexanoic acid) |
| 57 | Nmala | N-methyl-alanine |
| 58 | Nva | norvaline (or 2-aminopentanoic acid) |
| 59 | Obser | 0-benzylserine |

TABLE 3-continued

Coded and Non-Coded Amino Acids

| NO: | abbrev | name[s] |
|---|---|---|
| 60 | Obtyr | 0-benzyl-tyrosine |
| 61 | Oetyr | O-ethyltyrosine |
| 62 | Omser | O-methylserine |
| 63 | Omthr | 0-methyt-hreonine |
| 64 | Omtyr | 0-methyl-tyrosine |
| 65 | Orn | ornithine |
| 66 | Pen | penicillamlne |
| 67 | Pga | pyroglutamic acid |
| 68 | Pip | pipecolic acid |
| 69 | Sar | sarcosine |
| 70 | Tfa | 3,3,3-trifluoroalanine |
| 71 | Thphe | 6-hydroxydopa |
| 72 | Vig | L-vinylglycine |
| 73 | Aaspa | (−)-(2R)-2-amino-3-(2-aminoethylsulfonyl)propanoic acid dihydrochloride |
| 74 | Ahdna | (2S)-2-amino-9-hydroxy-4,7-dioxanonanolc acid |
| 75 | Ahoha | (2S)-2-amino-6-hydroxy-4-oxahexanoic acid |
| 76 | Ahsopa | (−)-(2R)-2-amino-3-(2-hydroxyethylsulfonyl)propanoic acid |

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a residue in a pHLIP sequence (corresponding to a location relative to SEQ ID NO: 3) is replaced with another amino acid residue from the same side chain family.

pHLIP Peptide is Monomeric pHLIP peptides, e.g., (SEQ ID NO: 4) are a water-soluble polypeptides based on the the bacteriorhodopsin C helix, which was found to insert across a membrane to form a stable transmembrane alpha helix. Peptide folding and membrane insertion are driven by a drop of pH from neutral or high (>7.4) to slightly acidic (7.0-6.5 and less) pHs. The apparent pK of insertion was found to be 6.0. pHLIP is a monomer in each of its three major states: unstructured and soluble in water (state I) at neutral pH, unstructured and bound to the surface of a membrane at neutral pH (state II), and inserted across the membrane as an α-helix at low pH (state III). In contrast, all pore forming peptides first form aggregates on the membrane surface and then "fall" into membrane and form pores. Thus, an additional advantage of the environmentally-sensitive compositions is their monomeric nature, e.g., they do not require assembly into a multimeric suprastructure like pore formers.

Delivery of Cargo Using pHLIP-liposomes

Although gold nanospheres and nanorods have been used for the enhancement of radiation therapy and for thermal ablation of tumors, delivery of enough gold material to cancer cells to produce the desirable effect has been a challenge. Gold nanoparticles attached to the N-terminus of pHLIP have been successfully delivered to tumors and accumulate on the surface of membrane of cancer cells. Another even more efficient way to deliver gold material (or other compounds) to tumor (or other cells characterized by low pH) is to use pHLIP-liposomes. pHLIP-liposomes are useful deliver to cells in a pH-dependent manner any compound, e.g., polar or hydrophobic compounds, that have been difficult to get into cells using other methods. In contrast to fusiogenic liposomes developed before for delivery, which can fuse with cellular membrane only in the absence of PEG coating, pHLIP can mediate fusion between lipid bilayer of plasma membrane or membrane of endosome/lysozome and liposomes made of non-fusogenic lipids and containing 10 mol % of PEG. pHLIP conjugated to the pegylated liposomes promotes pH-modulated: i) endocytotic uptake of liposomes by targeted cell, distortion of endosome compartment and release of lipids or liposome content into cytoplasm, and ii) direct liposomal fusion with plasma membrane and release of liposomal content into cytoplasm. pHLIP promotes mitochondrial delivery of R18 incorporated into liposome. As described in detail below, various assays were performed on liposomes in solution and on live cells to demonstrate that pHLIP mediates uptake of liposomes. The in vivo data shows high uptake of pHLIP-labeled liposomes by cancer cells.

In some embodiments, the present invention relates to the use of pHLIP technology for selective delivery of gold nanoparticles and liposomes to cancer cells in vivo. The data described herein demonstrate that gold nanoparticles attached to the N-terminus of pHLIP are delivered to tumors and accumulate on the surface of membrane of cancer cells. Distribution of gold nanoparticles in tumor was investigated by light microscopy after silver enhancement.

Toxicity

Toxicity is one of the most critical issues in the selection of any delivery agent. For example, the use of pore-forming membrane peptides as delivery agents is complicated by the toxicity associated with the formation of pores in cellular membranes in vivo. By contrast, the interaction of pHLIP with liposomes and cellular membranes at both neutral and low pHs does not lead to membrane leakage, and no cellular toxicity was seen over a range of peptide concentrations.

Selectivity of Targeting

The pH-dependent interaction of pHLIP with membranes allows selectivity in the targeting of acidic (less than pH 7.0) diseased tissue. As noted above, acidity and hypoxia are considered as universal cancer biomarkers, and pHLIP is used as an acidity-targeting probe. Besides cancer, many other pathological states, such as inflammation, ischemia, stroke, arthritis and others are characterized by acidity in the extracellular space, which may broaden the potential applications of pHLIP. In vivo fluorescence imaging in mice and rats demonstrated that pHLIP can target acidic tissues, such as kidneys, tumors of various sizes and origins, and anatomical sites of inflammation, e.g., arthritis, infection, atherosclerotic plaques. In addition to fluorescence imaging, PET (positron emission tomography) imaging of the acidic environment in human prostate tumors was performed using $^{64}$Cu-DOTA conjugated to pHLIP. PET studies demonstrated that the construct avidly accumulated in LNCaP and PC-3 tumors and that tumor uptake correlates with the differences in the bulk extracellular pH ($pH_e$) measured by MR spectroscopy. To manipulate the acidity of tissues, a buffer solution is administered to the subject systemically or local to the area in which a pH change is desired. In this manner, pHLIP-liposome-mediated delivery of a cargo compound is regulated, e.g., reduced or stopped. For example, administering bicarbonated water, which increases tissue pH, results in a reduction of tumor targeting by pHLIP.

Molecular Mechanism of pH-dependent Membrane Insertion of pHLIP

The transmembrane (TM) part of exemplary pHLIP peptides contain two Asp residues. At neutral pH these charged residues enhance peptide solubility and serve as anchors keeping the peptide at the surface of membrane, thereby preventing pHLIP partitioning into the hydrophobic membrane bilayer. A reduction of pH induces protonation of Asp residues, and as a result, the overall hydrophobicity of the peptide increases, enhancing the affinity of the peptide for the lipid bilayer core and triggering peptide folding and insertion. The replacement of the key Asp residues by Lys, Ala or Asn leads to the loss of peptide of pH-dependent membrane insertion, as measured in liposomes, red blood cells and confirmed by in vivo fluorescence imaging. The K-pHLIP peptide, where the two Asp residues in the transmembrane region are replaced with Lys residues, does not demonstrate tumor targeting. The Ala substitutions yield a peptide that aggregates in solution (but de-aggregates when it becomes diluted in bodily fluids or tissue upon administration to a subject), while the Lys and Asn substitutions give peptides that are too polar to insert either at neutral or low pH. The replacement of one of the Asp residues in the TM part of the peptide by a Glu residue results in a shift of pH of membrane insertion from 6.0 to 6.5. Replacement of both Asp residues by Glu results in enhancement of peptide aggregation and formation of elements of secondary structure on the bilayer surface at neutral pH (see Tables 1 and 2).

Data obtained using liposomes, cultured cells and mice confirmed that the mechanism of membrane entry of pHLIP is not mediated by endocytosis, interactions with cell receptors or pore formation; rather, the mechanism is the formation of a helix across the lipid bilayer, triggered by the increase of peptide hydrophobicity due to the protonation of negatively charged residues induced by low pH.

Solubility and Stability of pHLIP in Blood

Poor solubility due to aggregation is a typical property of membrane peptides, which has complicated studies and applications. Isolated or purified pHLIP, as any membrane peptide, also has a tendency to aggregate, especially at high concentrations and/or low pH. However, in aqueous solution at neutral pH pHLIP exists as a monomer at concentrations less than 30 µg/mL (~7.0 µM), as studied by fluorescence and CD spectroscopy measurements, size exclusion chromatography coupled with "on-line" laser light scattering, ultraviolet and refractive index detection (SEC-LS/UV/RI) and analytical ultracentrifugation experiments. When the solubility of the peptide is compromised as a result of mutations, the affinity of the peptide for a membrane and its overall conformational properties change. Thus, studies were undertaken to design pHLIP peptides that are optimized for clinical diagnostic and therapeutic use.

Figure 28:
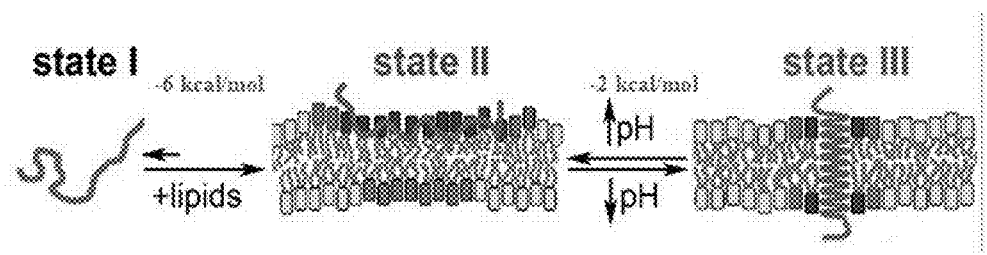
FIG. 28 is a diagram of states I, II, and III of pHLIP.

The oligomeric state of the peptide on the surface of a membrane (state II) and inserted into the lipid bilayer (state III) were evaluated by FRET performed with two different donor-acceptor probes attached to the N-terminus of the peptide. The data demonstrate that, at low concentrations, the peptide is monomeric in both states II and III (FIG. 28).

Peptide interactions with proteins, especially plasma proteins, and membranes determine the pharmacokinetics of the peptide at neutral pH. pHLIP demonstrates prolonged circulation in the blood (several hours), which is consistent with its ability to bind weakly to membrane surfaces at neutral and high pH, preventing the rapid clearance by the kidney expected for a small, soluble peptide. pHLIP binding to membranes is driven by hydrophobic interactions. If the peptide sequence were made more hydrophobic, tighter binding to red blood cells and epithelial cells and more aggregation in solution, and slower clearance and reduced bioavailability would occur. Making the peptide less hydrophobic accelerates clearance and prevents the peptide from finding its targets. Therefore, fine tuning of the solubility is an important property to optimize pHLIP performance in vivo.

Another important property is the stability of peptides in the blood, since proteases in the serum can degrade peptides consisting of L-amino acids within minutes. While polypeptides made from D-amino acids are much more stable, they are often unsuitable for specific receptor binding applications as a consequence of their altered chirality. Since the mechanism of pHLIP involves relatively nonspecific interactions with a fluid lipid bilayer, pHLIP peptides composed of L- or D-amino acids demonstrate the same biophysical and tumor targeting properties. This observation confirms the evidence that the pHLIP targeting does not require any specific molecular binding event. The only conspicuous difference is that D-pHLIPs form left-handed helices across membranes rather than the right-handed helices formed by L-pHLIPs.

EXAMPLES

Example 1 pHLIP-Mediated Delivery of Liposomes

The following regents and methods were used to generate the data described herein.

Lipids:
DOPE 1,2-dioleoyl-sn-glycero-3-phosphoethanolamine

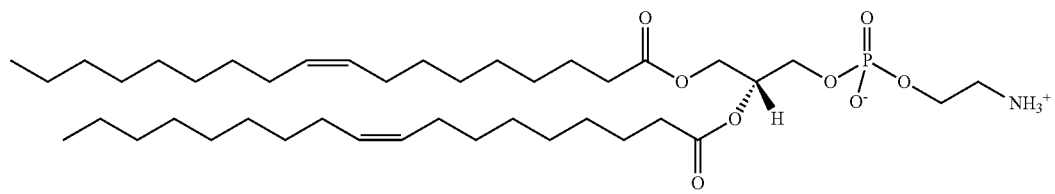 [SMILES: CCCCCCCC/C=C\CCCCCCCC(=O)OC[C@H](COP(=O)([O-])OCC[NH3+])OC(=O)CCCCCCC/C=C\CCCCCCCC]

DOPC
1,2-dioleoyl-sn-glycero-3-phosphocholine
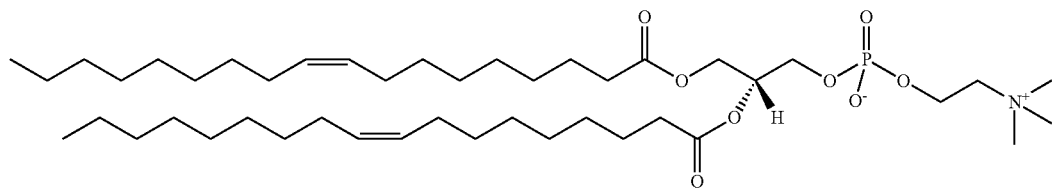 [SMILES: CCCCCCCC/C=C\CCCCCCCC(=O)OC[C@H](COP(=O)([O-])OCC[N+](C)(C)C)OC(=O)CCCCCCC/C=C\CCCCCCCC]
DSPE-PEG(2000) Maleimide
1,2-distearoyl-sn-glycero-3-phosphoethanolamine-N-[maleimide(polyethylene glycol)-2000](ammonium salt)
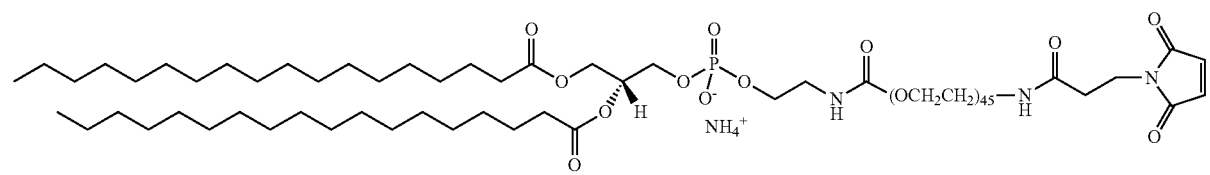
DSPE-PEG(2000)
1,2-diteaoy-sn-glycero-3-phosphoethanolamine-N-[methoxy(polyethylene glycol)-2000]
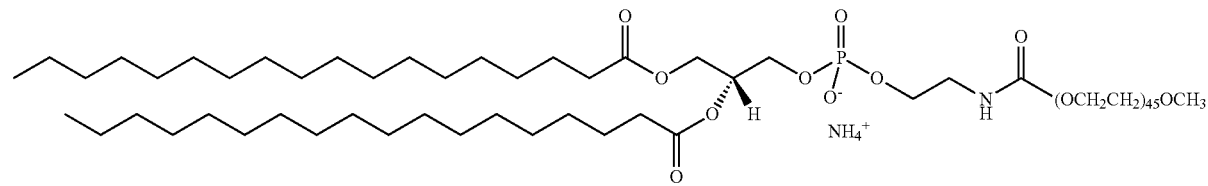
Fluorescein DHPE
N-(fluorescein-5-thiocarbamoyl)-1,2-dihexadecanoyl-sn-glycero-3-phosphoethanolamine, triethylammonium salt
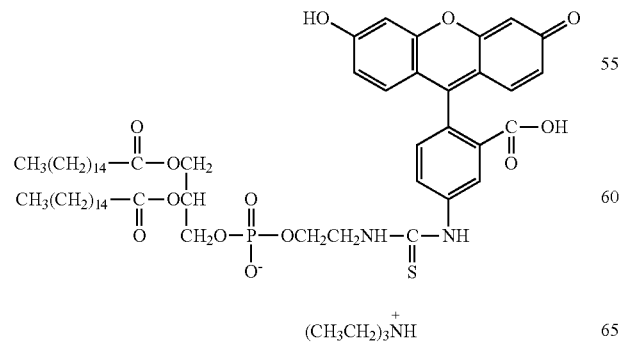

Rhod PE 1,2-dioleoyl-sn-glycero-3-phosphoethanolamine-N-(lissamine rhodamine B sulfonyl

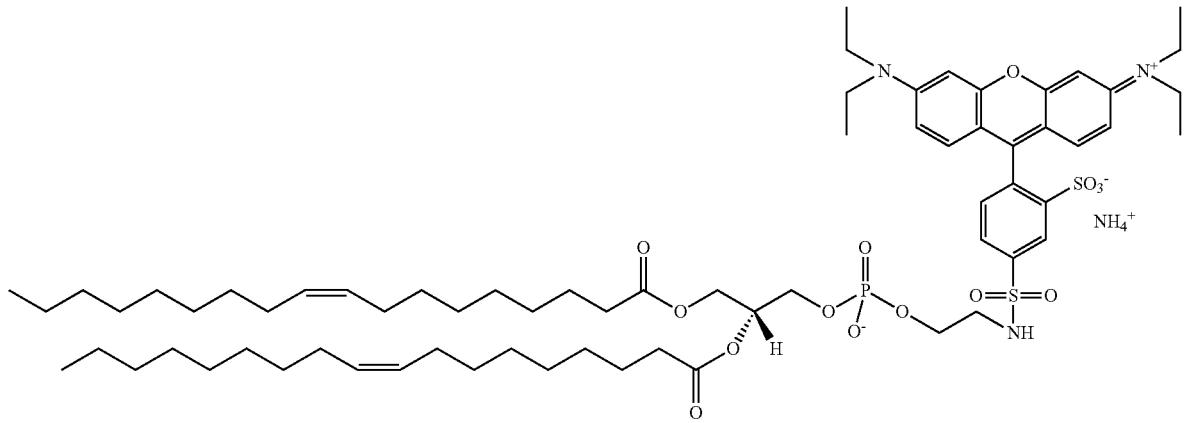

R18 (octadecyl rhodamine B chloride)

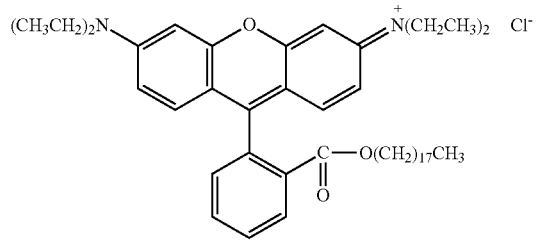

Conjugation of pHLIP with Lipids pHLIP containing Cys on the N-terminus and DSPE-PEG (2000) Maleimide lipids. Standard maleimide chemistry reaction was applied in methanol. (Reaction of thiol with maleimide.)

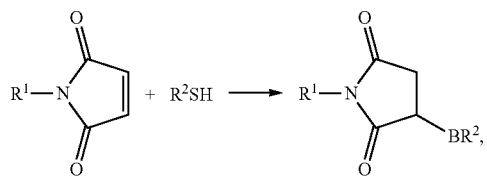

where
$R^1$—DSPE-PEG(2000) Maleimide (MW 2941)
$R^2$—cys-pHLIP (MW 4150)
$R^1$: $R^2$=1:1.5 in DMF or 1:1.2 in Methanol.

Figure 30:
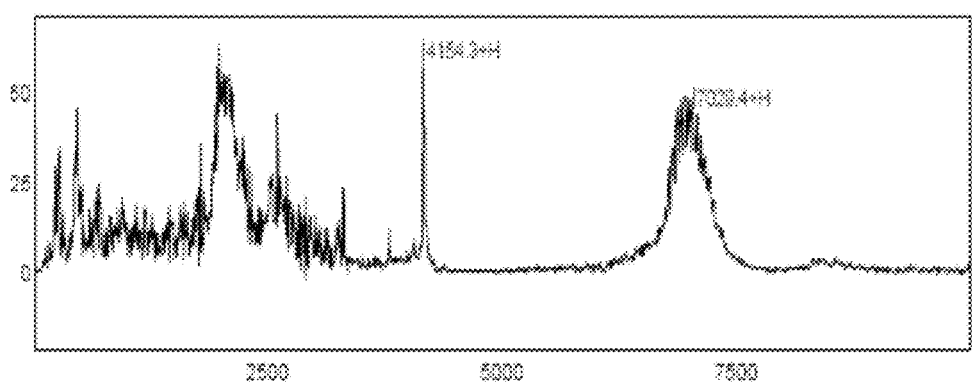
FIG. 30 is a line graph showing verification of reaction product by SELDI-TOF mass spectrometry.

The reaction product was verified by SELDI-TOF masspec. Expected mass of about 7 kDa was observed (FIG. 30).

Liposome Compositions Used in Experiments with Cells

| DOPC: | DOPC | 85 mol % |
| | DSPE-PEG | 5-10 mol % |
| | Fluorescent-lipids | 5 mol % |
| DOPC-pHLIP: | DOPC | 85 mol % |
| | DSPE-PEG | 0-5 mol % |
| | Fluorescent-lipid | 5 mol % |
| | DSPE-PEG-pHLIP | 0-5 mol % |
| DOPE: | DOPE | 85 mol % |
| | DSPE-PEG | 5-10 mol % |
| | Fluorescent-lipid | 5 mol % |
| DOPE-pHLIP: | DOPE | 85 mol % |
| | DSPE-PEG | 0-5 mol % |
| | Fluorescent-lipid | 5 mol % |
| | DSPE-PEG-pHLIP | 0-5 mol % |

Liposome Preparation

Liposomes were prepared by the thin film method (extrusion). A chloroform solution of the desired lipids (1 μmol) was evaporated using rotary evaporator, producing an even, thin film. The film was placed under a vacuum overnight to remove trace solvent impurities. This film was then hydrated in 1 mL 10 mM phosphate, 150 mM NaCl stock buffer solution via 10 freeze-thaw-vortex cycles. The resulting multilamellar liposome solution was then extruded 15 times through 100 nm polycarbonate filters and sterilized by filtering through 0.2 μm filter.

Cryo-electron Microscopy

Cryo-electron microscopy (cryo-EM) is a form of transmission electron microscopy (TEM) where the sample is studied at cryogenic temperatures (generally liquid nitrogen temperatures). It allows the observation of specimens that have not been stained or fixed in any way, showing them in their native environment.

FEI Vitrobot™ Mark IV is a fully automated vitrification robot for plunge-freezing of aqueous (colloidal) samples. For sample preparation, vitrification in liquid ethane was performed via Vitribot apparatus, with a single blot of 3 sec, an offset of −1, and drain and wait time of 1 sec. For imaging, sample was kept at −175° C. during imaging in a JEOL 2100 TEM with an accelerating voltage of 200 kV. Images were taken at 20,000× and 40,000×.

Cryo-TEM images of liposomes (DOPE, DOPE-pHLIP, DOPC, and DOPC-pHLIP) are shown in FIG. 19.

Inter-Liposome Fusion Assay pHLIP-mediated inter-liposome fusion was studied by an Octadecyl rhodamine B (R18) self-quenching assay. Liposomes labeled with R18 were mixed with various concentrations of unlabeled liposomes (POPC). During the process of dropping pH of solution, rhodamine fluorescence was monitored on the spectrofluorometer (FIG. 2).

The spectrofluorometer instrument was utilized. Slow kinetics—emission intensity measurement (excitation/emission: 556 nm/590 nm).

Steps:

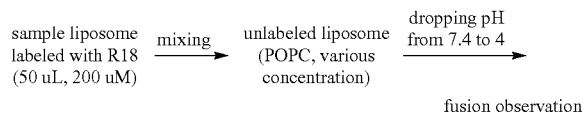

Figure 2B:
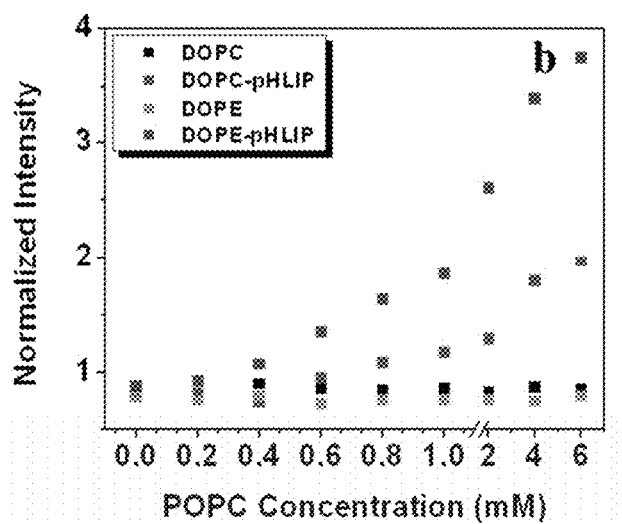
FIG. 2B is a dot graph showing that and increase in intensity of DPOC, DOPC-pHLIP compared to DOPE and DOPE-pHLIP when 200 uM of R18-labeled liposome was mixed with 6 mM of unlabeled POPC and when 200 uM of R18-labeled liposome was mixed with elevated concentration of unlabeled POPC (0-6 mM).
Figure 2C:
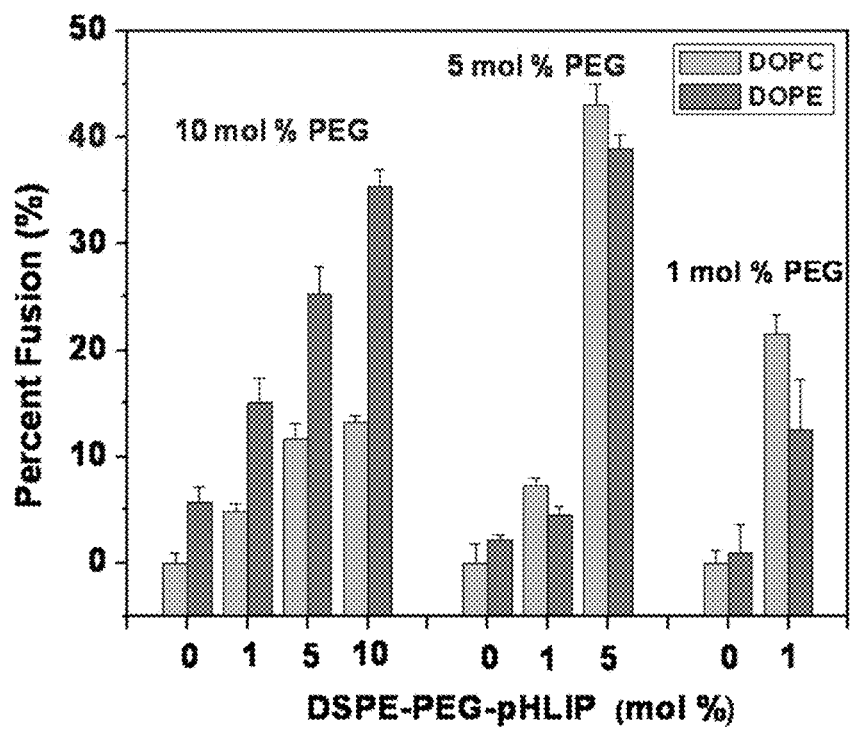
FIG. 2C is a bar chart showing that the amount of PEG-lipid or pHLIP-conjugated lipid contained in liposome affects the percentage of fusion.

The rhodamine fluorescence of pHLIP-liposomes (DOPE-pHLIP or DOPC-pHLIP) increased significantly after dropping pH from 8 to 4. 200 μM of R18-labeled liposome was mixed with 6 mM of unlabeled POPC (FIG. 2A1-2A2). 200 μM of R18-labeled liposome was mixed with elevated concentration of unlabeled POPC (0-6 mM) at pH 4 (FIG. 2B). The amount of PEG-conjugated lipid containing in liposome affects the percentage of fusion (FIG. 2C). For FIG. 2C, 200 μM of R18-labeled liposome was mixed with 6 mM of unlabeled POPC. The percentage calculations are as follows:

$$\text{Percentage of fusion} = \frac{FL_{pH} - FL_0}{FL_{MAX} - FL_0} \times 100\%,$$

where $FL_0$ is initial fluorescent intensity of liposome mixture at pH 8, $FL_{pH}$ is fluorescent intensity of liposome mixture at pH 4, $FL_{MAX}$ is fluorescent intensity of liposome mixture at pH 4 after freeze-thaw cycle.

Figure 2D:
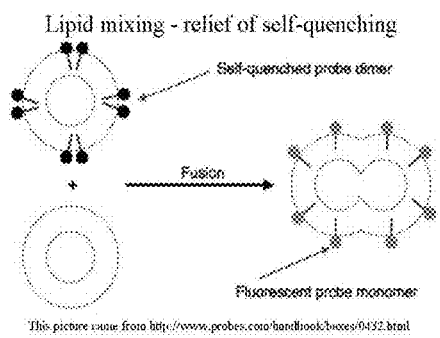
FIG. 2D is a schematic of the lipid fusion assay.
Figure 2E:
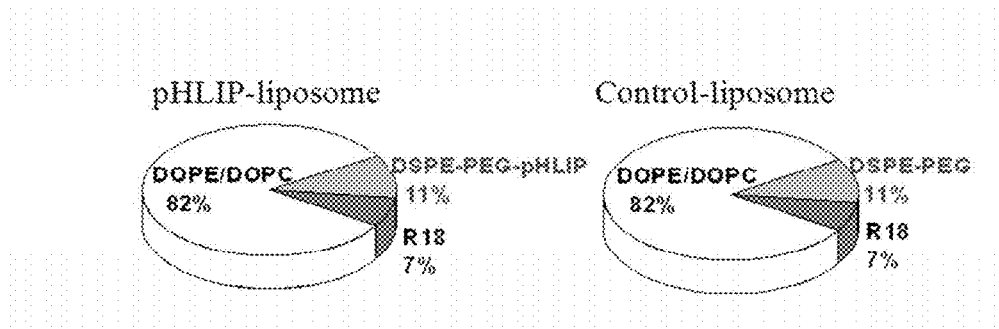
FIG. 2E is a schematic of the liposome composition.

The scheme of the fusion assay and liposome composition used in study are provided in FIGS. 2D and 2E.

Cell Suspension

Trypsinized cells were counted using a hemacytometer and diluted to 2×10⁵ cells/ml in serum-free low pH media. 20 nmol liposomes were incubated with 1×10⁵ cells in 500 μL serum-free low pH media for 15 min or 1 hr at 4° C. or 37° C. The cells were then pelleted by centrifugation (2000 rpm, 4 min) at 4° C. or 37° C. The cells were resuspended in 500 μL fresh serum-free low pH media and centrifuged a second time. This second pellet was resuspended in 100 μL same media. The cells were counted using cellometer: The sample was mixed well, and 2 μL of trypan blue was added to 18 μL of sample. 20 μL of this solution was loaded into disposable counting chamber (slide). The chamber was inserted into cellometer, and software was used to count cells. The cells were reseeded in collagen-coated cell dish for microscopy imaging.

Figure 14:
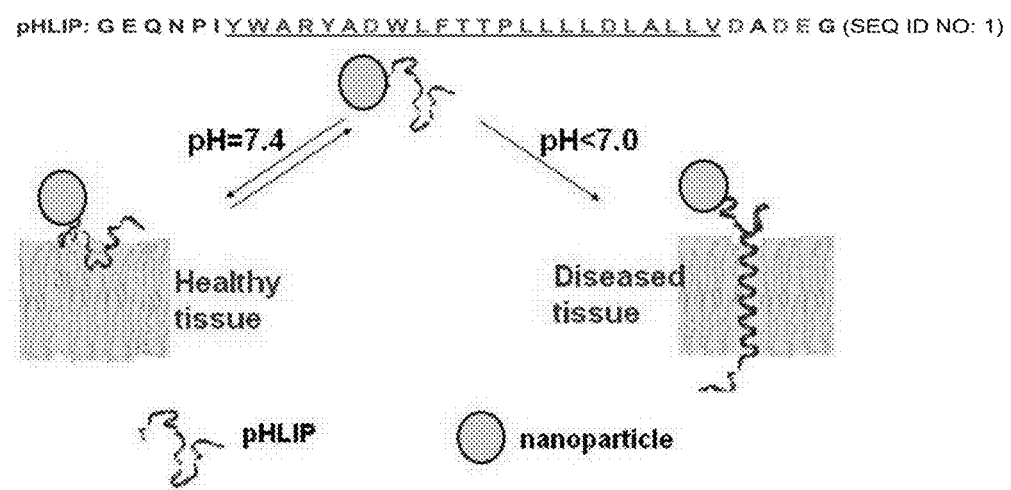
FIG. 14 is a schematic diagram showing that pHLIP (pH-Low-Insertion-Peptide) insertion into membrane occurs as a result of protonation of Asp/Glu residues due to a decrease of pH. Protonation enhances peptide hydrophobicity and increases its affinity for a lipid bilayer, which triggers peptide insertion and formation of transmembrane helix. Since many pathological states are associated with the development of elevated level of extracellular acidity (or low extracellular pH) pHLIP could be used for selective delivery of diagnostic and therapeutic agents to the cancer cells. Attachment of cargo molecules to the N-terminus.
Figure 15:
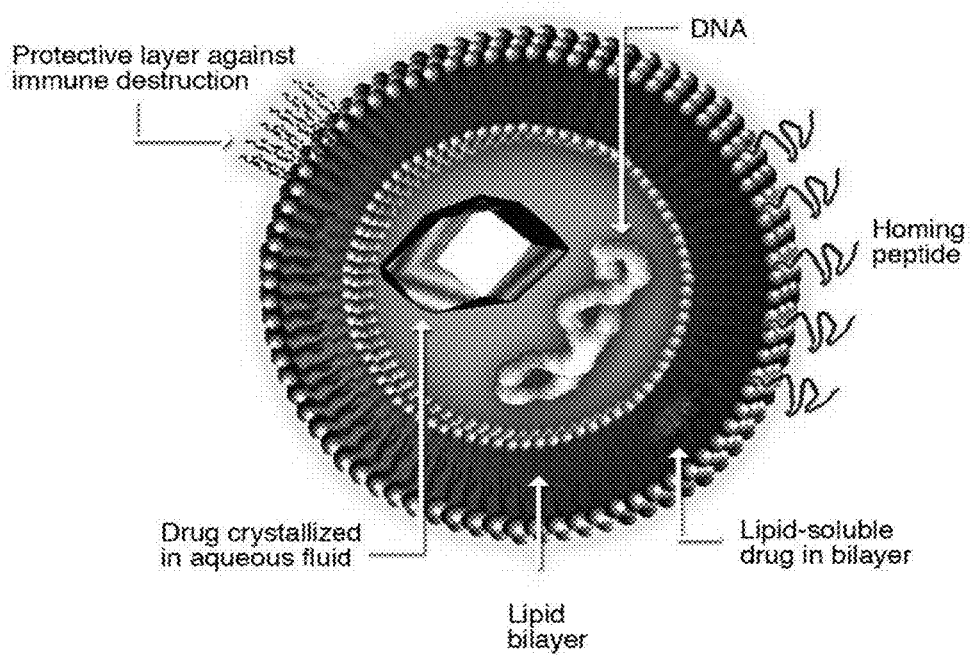
FIG. 15 is a schematic showing that liposomes are artificial vesicles primarily composed of phospholipid bilayers. Liposomes can be filled with drugs, and used to deliver drugs for cancer and other diseases. pHLIP technology may be used for selective delivery of liposomes to cancer cells.

Example 2 pHLIP Enhances Uptake of Liposomes by Cells pHLIP (pH-Low-Insertion-Peptide) insertion into membrane occurs as a result of protonation of Asp/Glu residues due to a decrease of pH. Protonation enhances peptide hydrophobicity and increases its affinity for a lipid bilayer, which triggers peptide insertion and formation of transmembrane helix. Since many pathological states are associated with the development of elevated level of extracellular acidity (or low extracellular pH), pHLIP-liposomes are ideally suited for selective delivery of diagnostic and therapeutic agents to the cancer cells. Attachment of cargo molecules to the N-terminus (FIG. 14).

One approach to deliver gold material (or cytotoxic compounds) to tumor is to use liposomes. In contrast to fusiogenic liposomes developed before for delivery, which can fuse with cellular membrane only in the absence of PEG coating, pHLIP mediates fusion between lipid bilayer of plasma membrane or membrane of endosome/lysozome and liposomes made of non-fusogenic lipids and containing 10 mol % of PEG. pHLIP conjugated to the pegylated liposomes promotes pH-modulated: i) endocytotic uptake of liposomes by targeted cell, distortion of endosome compartment and release of lipids or liposome content into cytoplasm; and ii) direct liposomal fusion with plasma membrane and release of liposomal content into cytoplasm. pHLIP promotes mitochondrial delivery of R18, incorporated into liposome. pHLIP was found to mediate uptake of liposomes. The in vivo data demonstrate high uptake of pHLIP-labeled liposomes by cancer cells.

Figure 3:
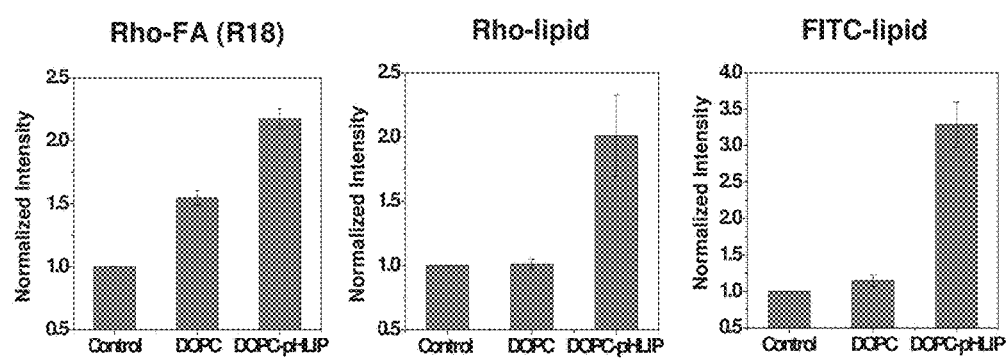
FIG. 3 is a series of bar charts demonstrating that pHLIP promotes cellular uptake of liposomes. Cellular uptake of pHLIP-decorated liposomes containing different fluorescent lipids (Rho-FA(R18), Rhodamine-PE, Fluorescein-DHPE) in comparison with the uptake of the same liposomes without pHLIP is shown.
Figure 4:
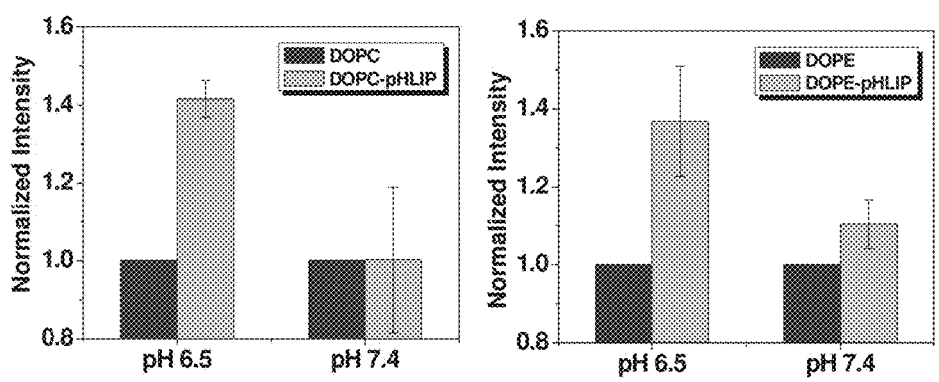
FIG. 4 is a series of bar charts showing cellular uptake of pHLIP-decorated liposomes at neutral and low pHs. pHLIP promotes cellular uptake of liposomes at low pH.
Figure 5:
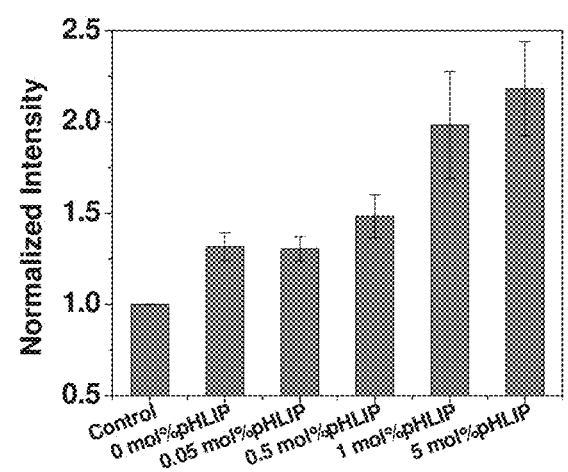
FIG. 5 is a bar chart demonstrating that cellular uptake of liposome increases with increase of amount pHLIP on the surface of liposome (DOPC lipids were used in study).
Figure 6:
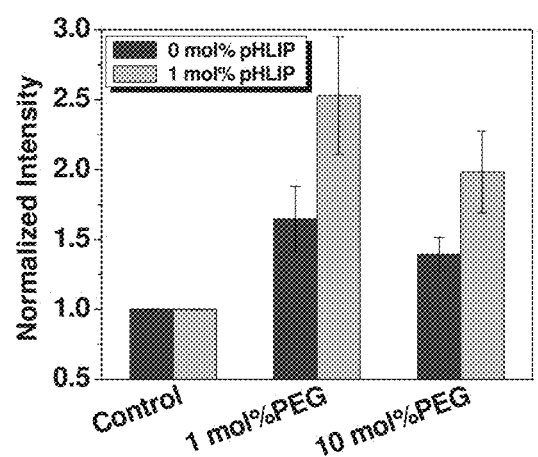
FIG. 6 is a bar chart showing cellular uptake of liposomes decorated with different amounts of PEG polymer (DOPC lipids were used in study).
Figure 7:
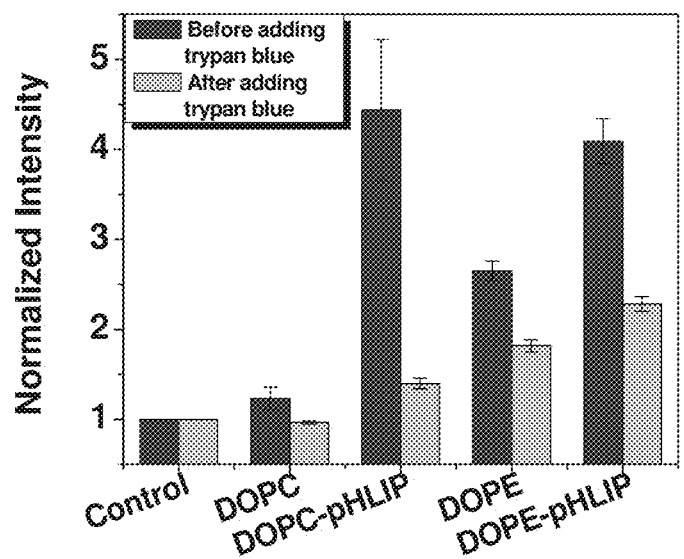
FIG. 7 is a bar chart showing the results of a trypan-blue fusion assay. After treatment of liposomes containing Fluorescein-lipid, the fluorescein fluorescence of cells was counted before and after adding trypan blue. Cell-impermeable trypan blue can quench fluorescein fluorescence only if fluorescein dye is located on the outer leaflet of cellular membrane facing to the extracellular space, which might occur only in a result of liposome-cell membrane fusion.
Figure 8:
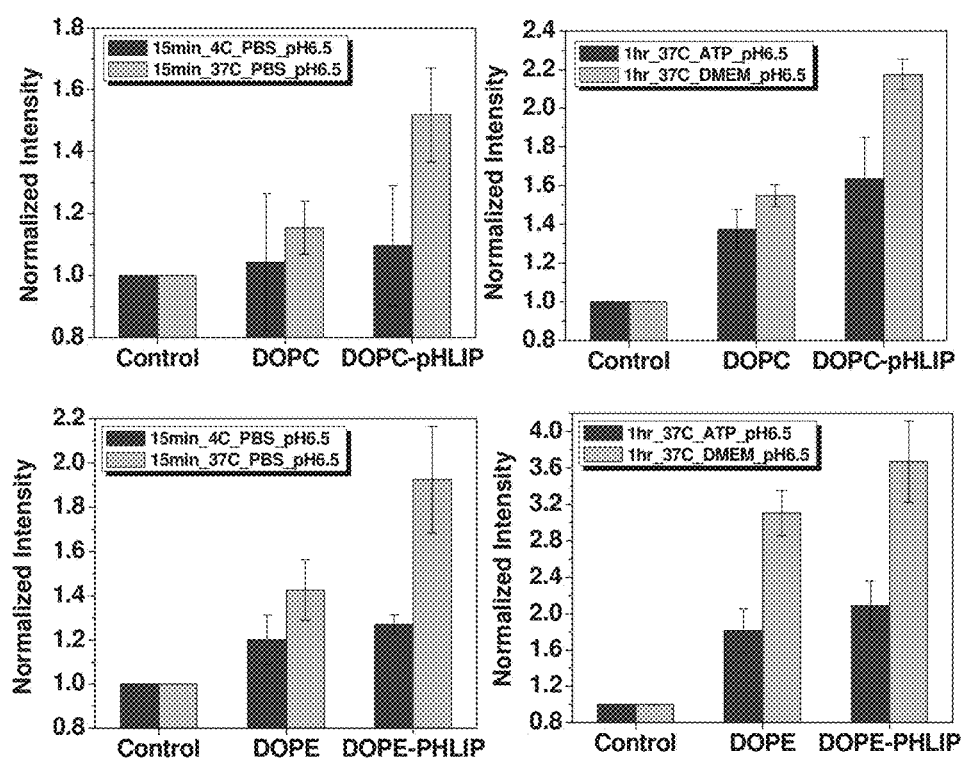
FIG. 8 is a series of bar charts showing the results of an endocytosis assay. Cell-liposome incubation was done for 15 or 60 min at 4° C. or 37° C. in different media (PBS, DMEM, ATP-depletion medium). Low temperature and ATP-depletion medium were used to reduce endocytotic uptake.

Cell uptake studies were performed as follows: cells in suspension were treated with 40 uM of fluorescently labeled pHLIP-liposomes (DOPE-pHLIP or DOPC-pHLIP) and control-liposomes (DOPE or DOPC) under different conditions, after washing, fluorescence of cells was counted by cellometer. (a) Liposomes containing different fluorescent lipid (Rho-FA(R18), Rhodamine-PE, Fluorescein-DHPE) were tested (FIG. 3). pHLIP-liposomes show high cell uptake. (b) Cells were incubated with R18-labeled liposomes in different pH of medium (FIG. 4). Liposome containing different amount of pHLIP-conjugated lipids (c; FIG. 5) and PEG-lipids (d; FIG. 6) were also investigated. (e) Trypan blue quenching assay: After treatment of liposomes containing Fluorescein-lipid, the FITC-fluorescence of cells was counted before and after adding trypan blue (FIG. 7). Cell-impermeable trypan blue can quench FITC fluorescence only if FITC dye is located on the outer leaflet of cellular membrane facing to the extracellular space, which might occur only in a result of liposome-cell membrane fusion. (f) Endocytosis assay: cells in suspension were incubated with liposomes for 15 or 60 min at 4° C. or 37° C. in different media (PBS, DMEM, ATP-depletion medium). Low temperature and ATP-depletion medium are used to reduce endocytotic uptake. The results are presented in FIG. 8. Thus, the data indicated that pHLIP enhanced uptake of liposomes by cells, and the primary pathway of liposome uptake was endocytosis.

A549 cell suspension (10×10⁵) was treated with R18 containing liposome (20 nmol) in 500 μL of serum-free low pH media for 1 hour at 37 C. The cells were pelleted by centrifugation (2000 rpm, 4 min) and resuspended in fresh DMEM. The cells were reseeded in collagen-coated cell dishes (FIG. 20). The light images (a, c) and fluorescent images (b, d) were taken after 4 days incubation. pHLIP-containing liposome (d) showed much higher cell uptake than the control liposome (b), which did not contain pHLIP.

Figure 9:
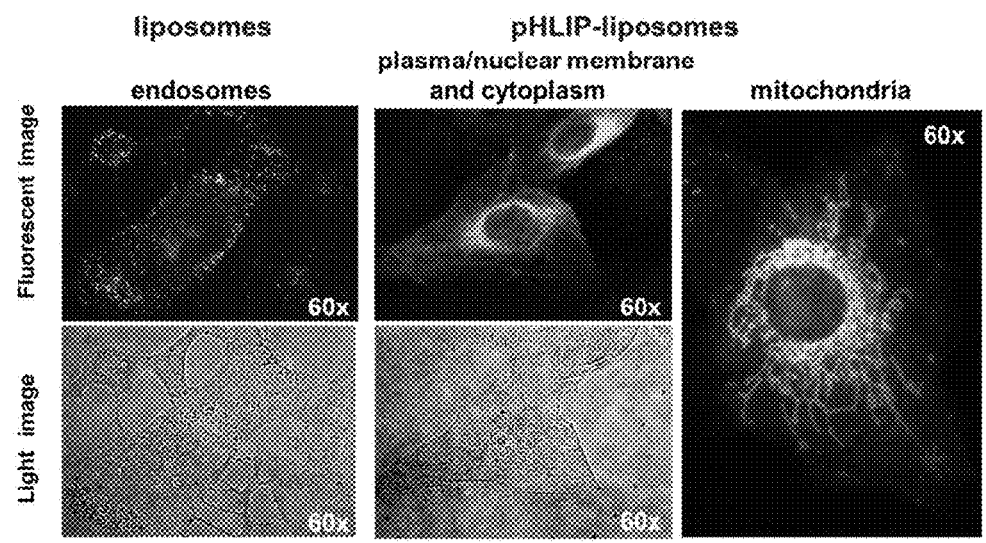
FIG. 9 is a series of photomicrographs demonstrating cellular localization of fluorescent fatty acids (R18) incorporated into liposomes containing PEG polymers and pHLIP or no pHLIP on the surface (non-fusogenic DOPC lipids were used in study). In case of liposomes, fluorescent signal was mostly localized in endosomes, while pHLIP promotes distortion of plasma and endosome membranes and release of R18-labeled FA into cytoplasm and targeting of mitochondria. All images are taken from live cells under inverted fluorescence microscopy at 60× objective magnification.
Figure 10:
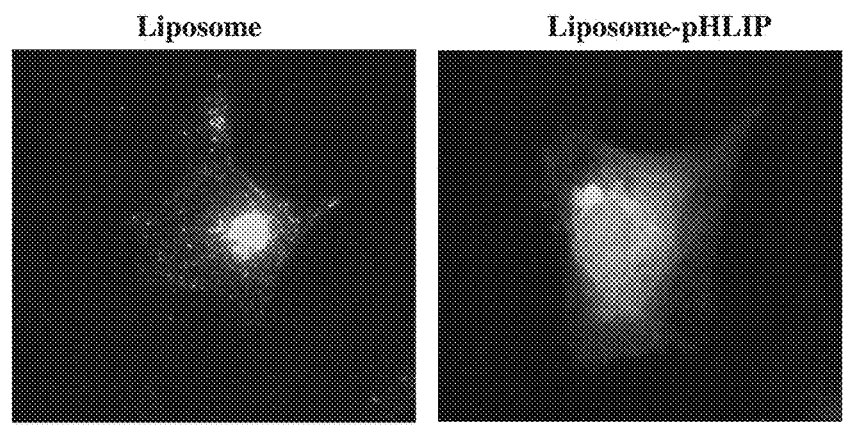
FIG. 10 is a series of photomicrographs showing cellular localization of fluorescent lipids (Rho-PE) incorporated into liposomes containing PEG polymers and pHLIP or no pHLIP on the surface (non-fusogenic DOPC lipids were used in study). In case of liposomes, fluorescent signal was mostly localized in endosomes, while pHLIP promotes distortion of plasma and endosome membranes and release of lipids into cytoplasm. All images are taken from live cells under inverted fluorescence microscopy at 60× objective magnification.
Figure 11A:
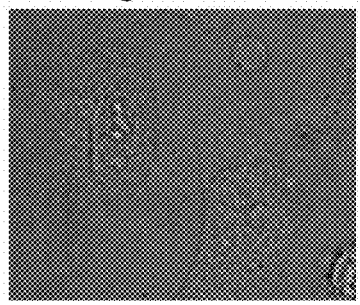
FIG. 11A is a photomicrograph showing cellular localization of fluorescent lipids (FITC (fluorescein)-PE) incorporated into liposomes containing PEG polymers and pHLIP.
Phase contrast image of cells treated with FITC-liposome-pHLIP is presented.
Figure 11B:
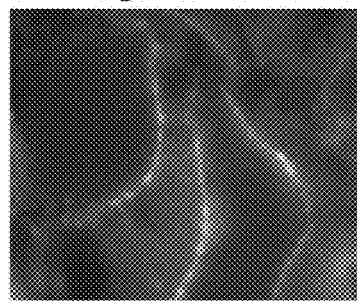
FIG. 11B is a photomicrograph showing cellular localization of fluorescent lipids (FITC (fluorescein)-PE) incorporated into liposomes containing PEG polymers and pHLIP. Fluorescent image of cells treated with FITC-liposome-pHLIP is presented. Staining of plasma membrane is evident.
Figure 11C:
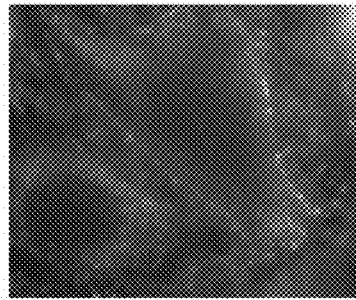
FIG. 11C is a photomicrograph showing cellular localization of fluorescent lipids (FITC (fluorescein)-PE) incorporated into liposomes containing PEG polymers and pHLIP. Fluorescent image of cells treated with FITC-liposome-pHLIP is presented. Staining of plasma membrane is evident. Co-localization of fluorescein fluorescence is observed.
Figure 11D:
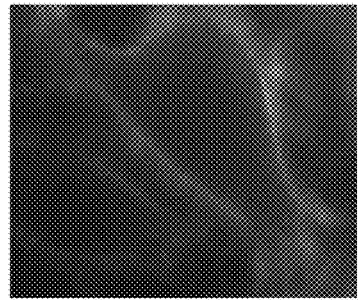
FIG. 11D is a photomicrograph showing cellular localization of fluorescent lipids (FITC (fluorescein)-PE) incorporated into liposomes containing PEG polymers and pHLIP. Fluorescent image of cells treated with FITC-liposome-pHLIP is presented and plasma membrane staining of red-fluorescent Alexa Fluor594 wheat germ agglutinin is observed.

Example 3 pHLIP Promotes Distortion of Plasma and Endosome Membranes, the Release of R18-Labeled FA into the Cytoplasm, and Targeting of Mitochondria After cellometer counting, cells were reseeded in collagen-coated cell dishes for microscopy imaging. Cellular localization of fluorescent fatty acids (R18) incorporated into liposomes containing PEG polymers and pHLIP or no pHLIP on the surface (non-fusogenic DOPC lipids were used in study). In case of liposomes, fluorescent signal was mostly localized in endosomes, while pHLIP promotes distortion of plasma and endosome membranes and release of R18-labeled FA into cytoplasm and targeting of mitochondria. FIG. 9 shows the localization of Rho-labeled liposome in cells.

FIG. 11 shows images of Fluorescein-labeled liposomes fused with a cellular membrane. FIG. 11(a) phase contrast; (b) FITC. Co-localization of FITC-liposome (c) and plasma membrane staining of red-fluorescent Alexa Fluor594 wheat germ agglutinin (d). The data demonstrate that lipids are exchanged as a result of fusion with the plasma membrane or membrane of the endosomal compartment, thereby reaching the plasma membrane. Thus, the methods described herein promote the delivery and release of agents that are encapsulated inside a pHLIP-liposome or attached to lipids of the pHLIP-liposome to the cytoplasm of a cell.

Figure 12:
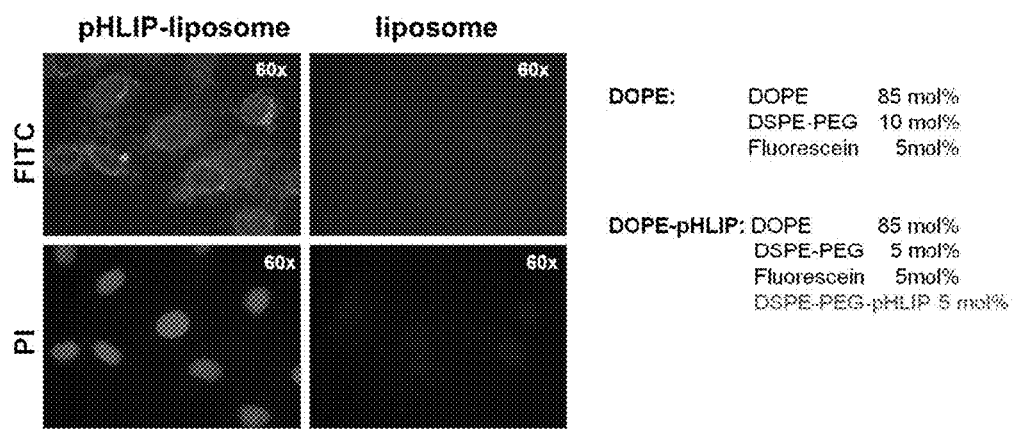
FIG. 12 is a series of photomicrographs showing pHLIP mediated release of PI from liposomes. The propidium iodide (PI) was encapsulated in Fluorescein-labeled liposomes. 10 nmol of liposome were incubated with cells attached to the collagen in 100 uL of low pH media for 1 hr at 37 C.

FIG. 12 shows the results of a liposome encapsulation experiment (delivery of propidium iodide to the nucleus). The propidium iodide (PI; 4 mM) was encapsulated in Fluorescein-labeled liposomes (FIG. 12). 10 nmol of liposome were incubated with cells attached to the collagen-coated cell dish in 100 μL of low pH media for 1 hr at 37° C. The release of PI from pHLIP-liposomes was observed.

Figure 16:
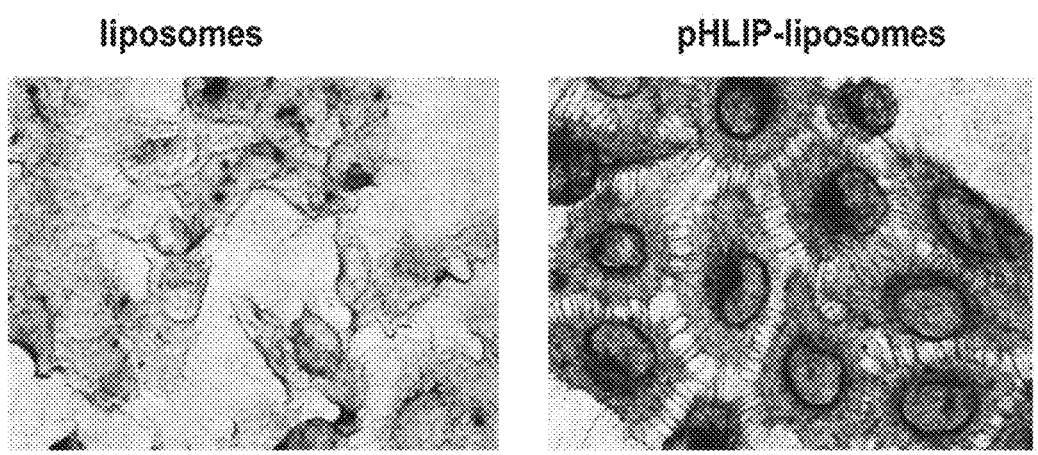
FIG. 16 shows two types of liposomes (100 nm in diameter), one of which was carrying 5 mol % of pHLIP peptides and the other was not. Both liposomes contained 5 mol % of nanogold-lipids and 10 mol % PEGylated lipids. Cells were treated with two types of liposomes separately, washed, fixed. After fixation, cells were treated with silver enhancement solution and analyzed under the light microscope. Nanogold-lipids were mostly localized on the plasma and nuclear membranes of cells treated with pHLIP-liposomes

FIG. 16 shows two types of liposomes (100 nm in diameter), one of which was carrying 5 mol % of pHLIP peptides and the other was not. Both liposomes contained 5 mol % of nanogold-lipids and 10 mol % PEGylated lipids. Cells were treated with two types of liposomes separately, washed, fixed. After fixation, cells were treated with silver enhancement solution and analyzed under the light microscope. Nanogold-lipids were mostly localized on the plasma and nuclear membranes of cells treated with pHLIP-liposomes (FIG. 16).

Figure 21:
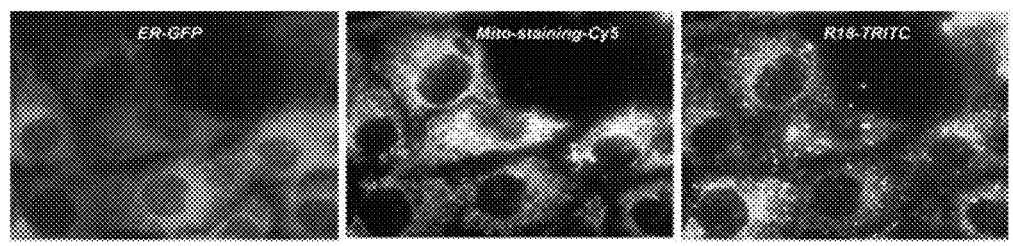
FIG. 21 is a series of photomicrographs showing ER labeling, mitochondria staining, and R18-liposome uptake in A549 cell suspension treated with R18 containing liposome.

A549 cell suspension (10×10$^5$) was treated with R18 containing liposome (20 nmol) in 500 uL of PBS (pH6.2) for 15 min at 37 C. The cells were pelleted by centrifugation (2000 rpm, 4 min) and resuspended in fresh DMEM. Then the cells were reseeded in collagen-coated cell dishes. After 4 days incubation, endoplasmic reticulum (ER) and mitochondria were labeled by fluorescent dyes of ER-Tracker and Mito-Tracker, respectively. The fluorescent images were taken with the filter setting of GFP, Cy5 and TRITC, corresponding to ER labeling, mitochondria staining and R18-liposome uptake (FIG. 21).

Example 4 pHLIP Promotes Uptake of Liposome in Low pH Extracellular Environment of Tumors

Figure 13:
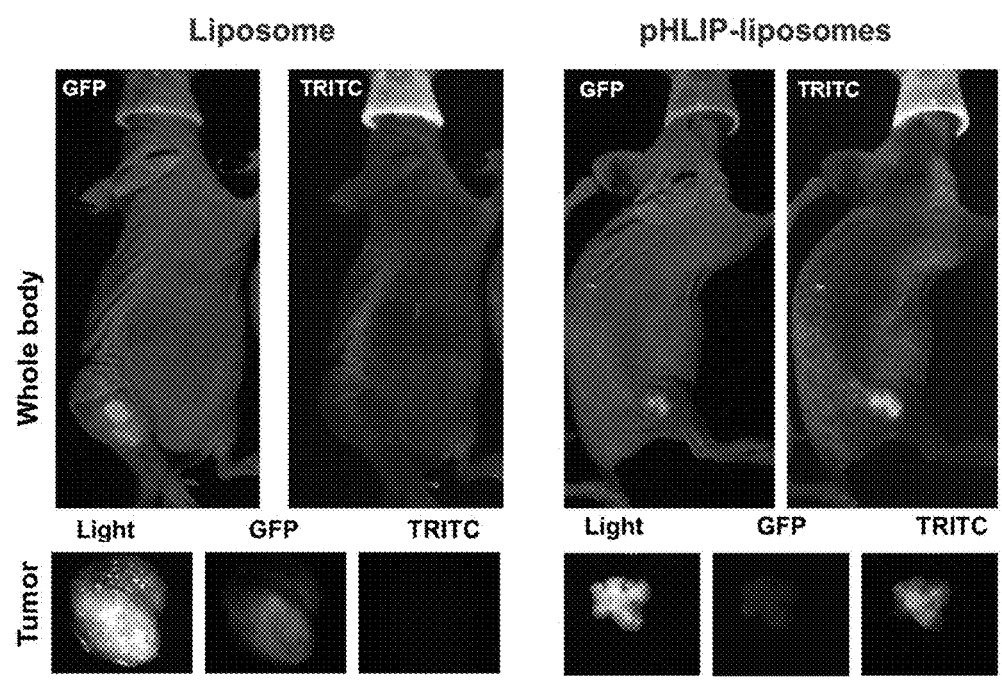
FIG. 13 is a series of photomicrographs showing that pHLIP promotes liposome uptake in low pH extracellular environment of tumors. Liposomes containing Rho-PE lipids, were given as a single intro-tumoral injection into mice with tumors established by subcutaneous injection of HeLa-GFP cancer cells. Mice were sacrificed at 24 hours post-injection, and tumors were collected. Whole-body and tumor images were taken on Kodak Imager.

Liposomes, containing Rho-PE lipids, were given as a single intra-tumoral injection into mice with tumors established by subcutaneous injection of HeLa-GFP cancer cells. Mice were sacrificed at 24 hours post-injection, and tumors were collected. Whole-body and tumor images were taken on Kodak in vivo imaging system. As shown in FIG. 13, pHLIP promoted liposome uptake in low pH extracellular environment of tumors, following IV injection of the fluorescent- and gold-containing liposomes.

Figure 17A:
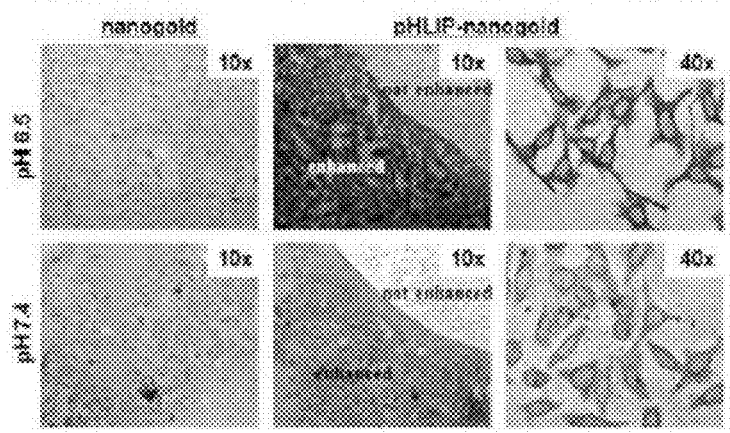
FIG. 17A is a series of photomicrographs showing pHLIP mediated cell staining by nanogold. HeLa-GFP cells were incubated with pHLIP-nanogold and nanogold particles at neutral and low pHs, washed, fixed and enhanced by silver then visualized under light microscope. The highest uptake was observed at low pH in presence of pHLIP.
Figure 17B:
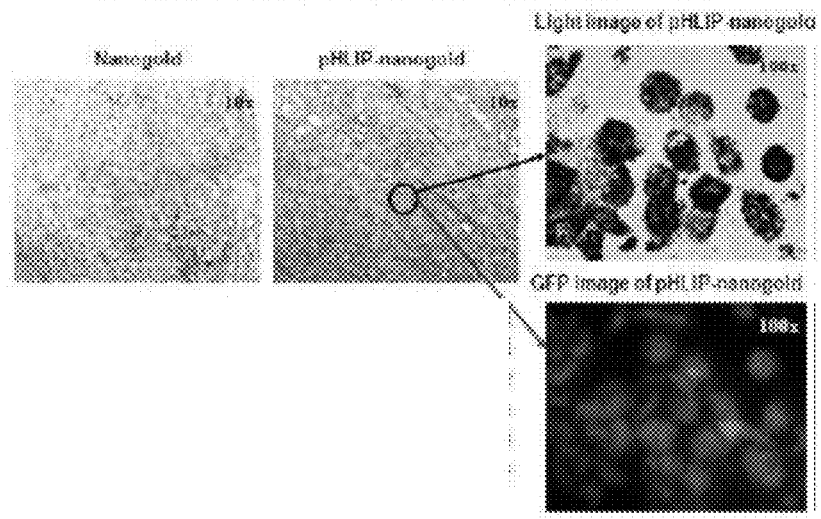
FIG. 17B is a series of photomicrographs demonstrating nanogold particles distribution in tumors. Tumor sections collected from mice that received a single iv injection of pHLIP-nanogold. Nanogold particles were treated with silver enhancement solution and visualized under the microscope. Nanogold particles delivered to tumor by pHLIP were localized on cancer cells identified by GFP fluorescence.
Figure 18:
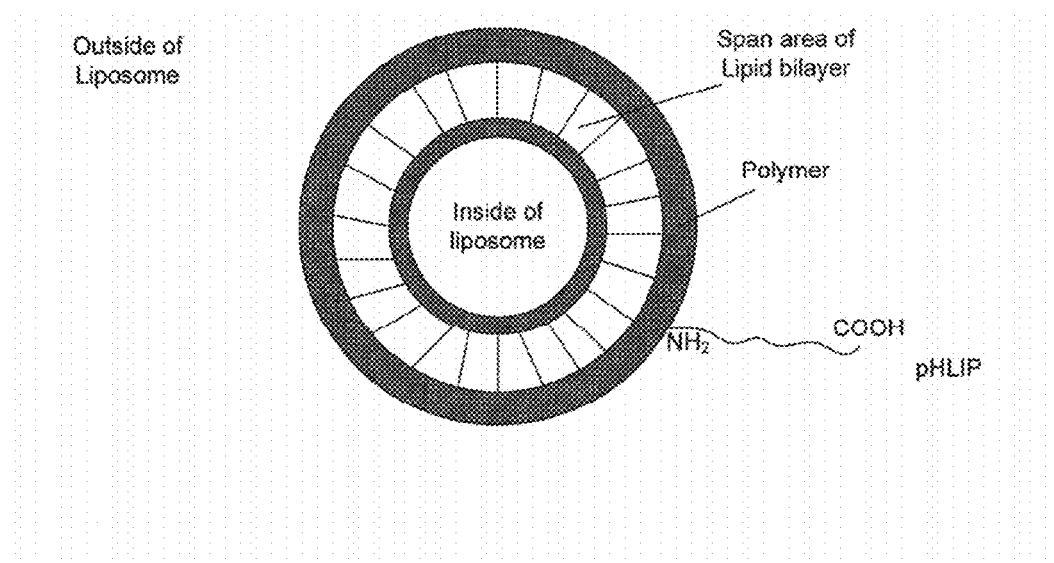
FIG. 18 provides an illustration of a liposome of one embodiment in which the lipid bilayer of the liposome is comprised of a polymer-pHLIP (e.g., PEG-pHLIP) is anchored into the liposomal membrane. The polymer is attached to the N-terminus of the pHLIP polypeptide. The pHLIP polypeptide is wholly outside the lipid bilayer.
Figure 19A:
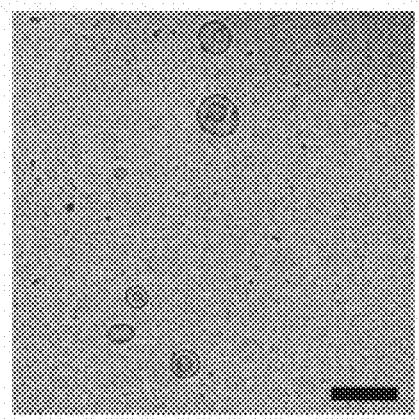
FIG. 19A is a photomicrograph of a Cryo-TEM image of DOPE liposomes.
Figure 19B:
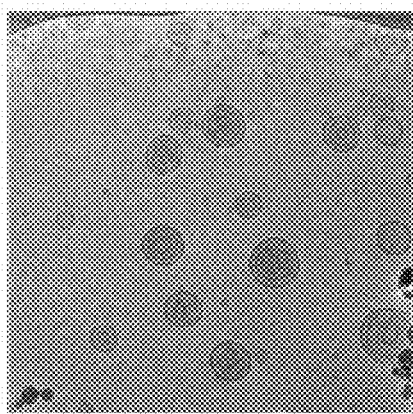
FIG. 19B is a photomicrograph of a Cryo-TEM image of DOPE-pHLIP liposomes.
Figure 19C:
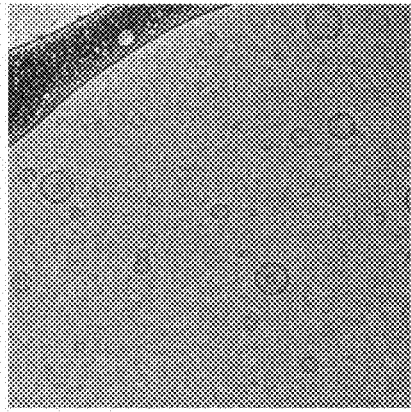
FIG. 19C is a photomicrograph of a Cryo-TEM image of DOPC liposomes.
Figure 19D:
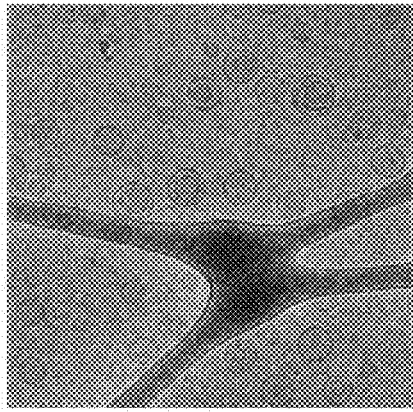
FIG. 19D is a photomicrograph of a Cryo-TEM image of DOPC-pHLIP liposomes.
Figure 20A:
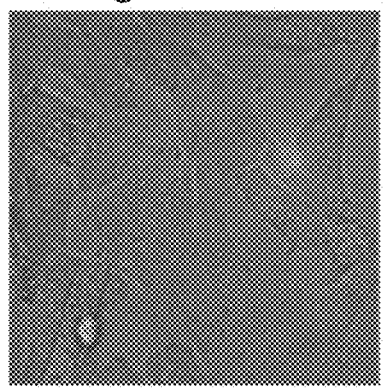
FIG. 20A is a photomicrograph showing pHLIP liposome cellular uptake. The light image was taken after 4 days incubation.
Figure 20B:
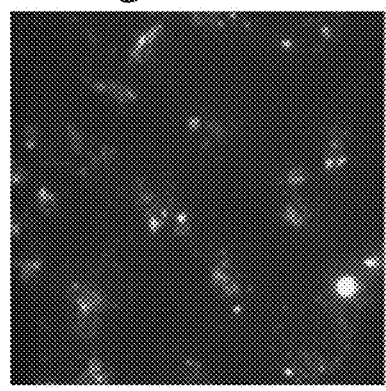
FIG. 20B is a photomicrograph showing pHLIP liposome cellular uptake. The fluorescent image was taken after 4 days incubation.
Figure 20C:
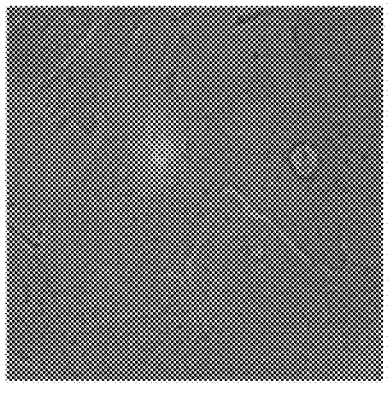
FIG. 20C is a photomicrograph showing pHLIP liposome cellular uptake. The light image was taken after 4 days incubation.
Figure 20D:
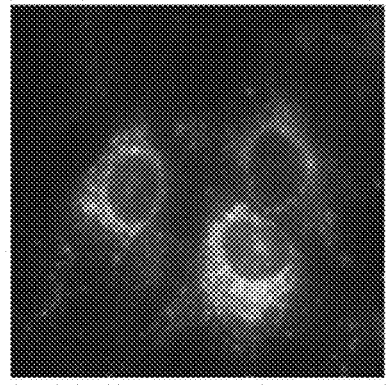
FIG. 20D is a photomicrograph showing pHLIP liposome cellular uptake. The fluorescent image was taken after 4 days incubation.

HeLa-GFP cells were incubated with pHLIP-nanogold and nanogold particles at neutral and low pHs, washed, fixed and enhanced by silver then visualized under light microscope. The highest uptake was observed at low pH in presence of pHLIP (FIG. 17A). Tumor sections collected from mice received single iv injection of pHLIP-nanogold and nanogold particles were treated with silver enhancement solution and visualized under the microscope. Nanogold particles delivered to tumor by pHLIP were localized on cancer cells identified by GFP fluorescence (FIG. 17B).

These data indicate that pHLIP-liposomes demonstrate enhanced uptake by cells in environments characterized by low pH (pH<7) compared to liposomes that do not contain pHLIP.

Example 5 pHLIP-Mediated Delivery of Lipsomal Ceramide to Cancer Cells

Figure 22:
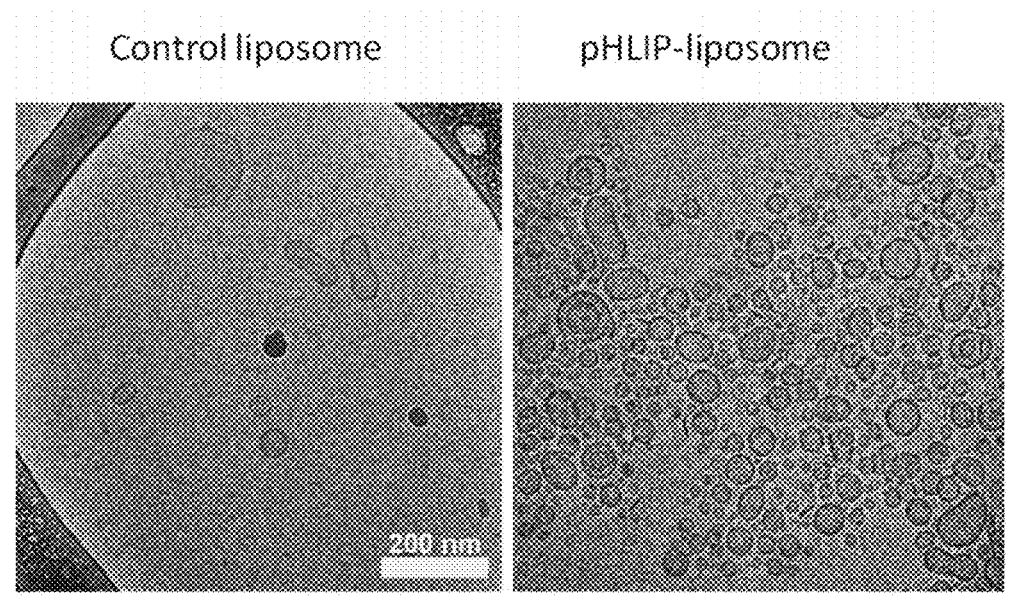
FIG. 22 is a series of photomicrographs of cryo-TEM images of ceramide-containing liposomes.

An exemplary ceramide formulation is provided below. Cryo-TEM images of ceramide-containing liposomes are shown in FIG. 22. The size and shape (round) of the particles indicate that ceramide liposomes were formed.

|  | Control-liposome | pHLIP-liposome |
| --- | --- | --- |
| DOPC | 37 mol % | 37 mol % |
| DOPE | 17.5 mol % | 17.5 mol % |
| DSPE-PEG$_{2000}$ | 7.5 mol % | 2.5 mol % |
| DSPE-PEG$_{2000}$-pHLIP | 0 mol % | 5 mol % |
| C8-PEG$_{750}$ | 7.5 mol % | 7.5 mol % |
| C6-ceramide | 30 mol % | 30 mol % |
| R18 | 0.5 mol % | 0.5 mol % |

Liposome Size Measurement

Figure 23A:
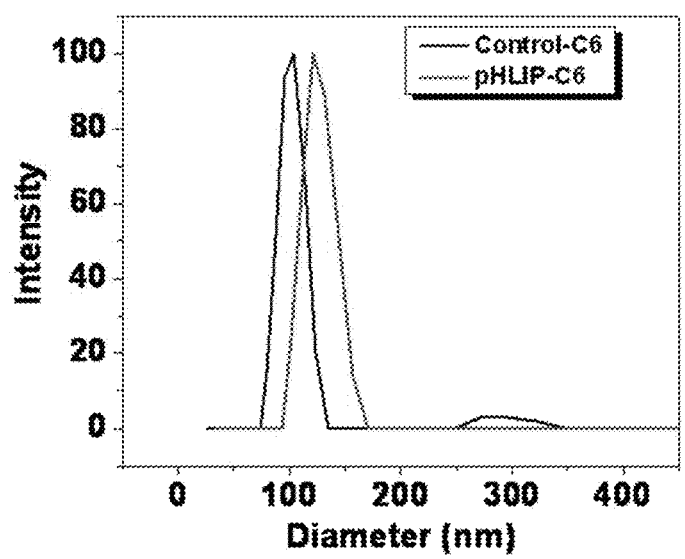
FIG. 23A is a line graph showing the diameter of control-liposome and pHLIP-liposome are 104 nm and 125 nm, respectively.
Figure 23B:
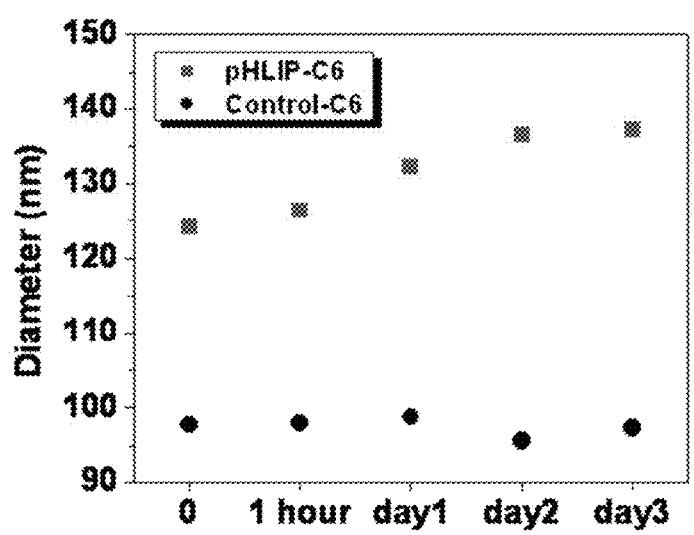
FIG. 23B is a dot plot showing that the size of control-liposome is stable after 3 days, while the size of pHLIP-liposome increases slightly.

The size of liposome was measured by using Dynamic Light Scattering (Zetasizer Nano ZS). The diameters of control-liposome and pHLIP-liposome are 104 nm and 125 nm, respectively (FIG. 23 A). After 3 days monitoring, the size of control-liposome is stable, while the size of pHLIP-liposome increased slightly (FIG. 23B).

Inter-liposome Fusion Assay of Ceramide Liposome

The fusion assay was performed as described in Example 1 and FIG. 2D.

| ISS Settings: | |
| --- | --- |
| $\lambda_{ex}$ = 556 nm | $\lambda_{em}$ = 590 nm |
| $\theta_{ex}$ = 54.7° | $\theta_{em}$ = 0.0° |
| Slit$_{ex}$ = 0.5 mm | Slit$_{em}$ = 1.0 mm |

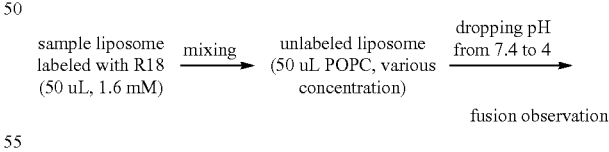

Figure 24A:
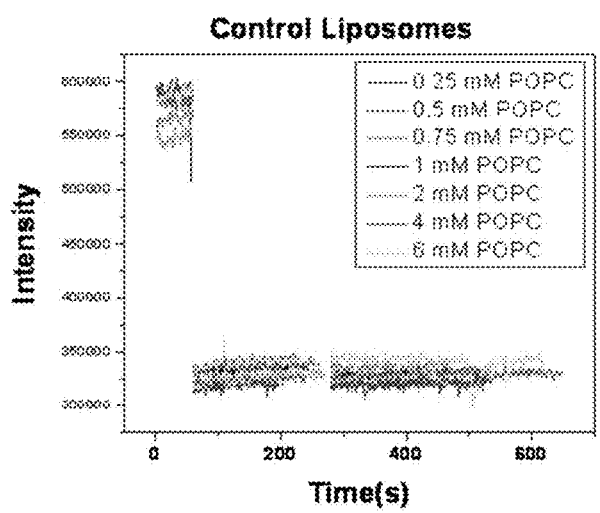
FIG. 24A-B are scans showing that there is no fusion of liposomes if pHLIP is not attached to the surface (no increase of fluorescence at low pH).
Figure 24B:
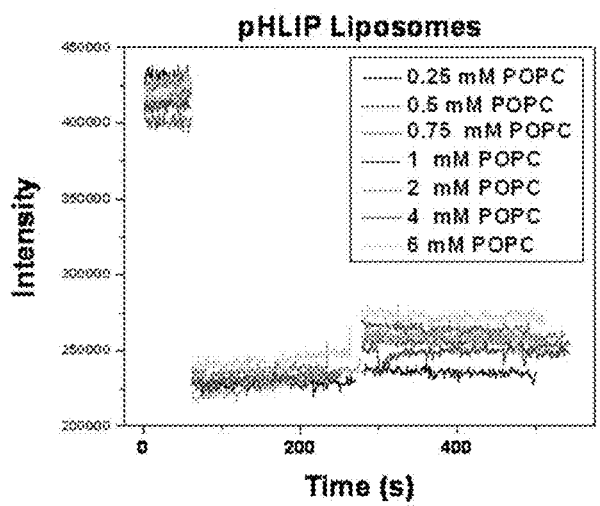
Figure 24C:
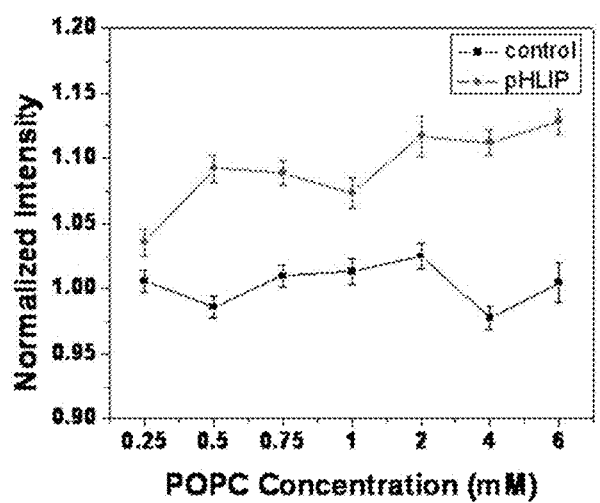
FIG. 24C is a line graph showing a summary of the data in FIGS. 24A and 24B. The black line shows no increase of fluorescence for the control experiment, and the red line shows that fluorescence increases in case of pHLIP-coated liposomes.

The results are presented in FIG. 24. FIG. 24A shows that there is no fusion of liposomes if pHLIP is not attached to the surface (no increase of fluorescence at low pH). FIG. 24B shows that there is an increase of fluorescence when pHLIP-coated liposomes are mixed with POPC liposomes, which indicates fusion of liposomes. Thus, pHLIP promotes fusion only at low pH. FIG. 24C is a summary of FIGS. 24A and 24B. The black line shows no increase of fluorescence for control experiment, and the red line shows that fluorescence increases in case of pHLIP-coated liposomes. The methods for this experiment were described in relation to FIG. 2 above: however, the amount of Rho-FA is much less (0.5 mol %) for FIG. 24 than FIG. 2 (5 mol %). Therefore, the increase of fluorescence is much less in FIG. 24 comparison to FIG. 2.

Figure 25:
FIG. 25 is a schematic of pHLIP-mediated delivery of liposomal ceramide to cells.
Figure 25:
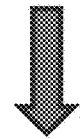
Figure 25:

A schematic of pHLIP-mediated Delivery of Liposomal Ceramide to Cells is provided in FIG. 25.

Figure 26:
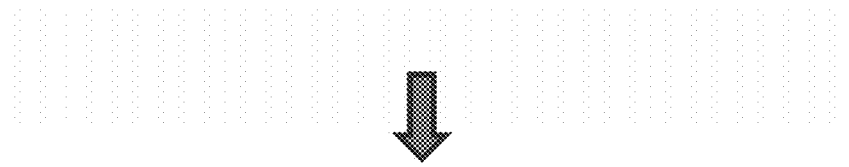
FIG. 26 is a schematic of pHLIP-mediated delivery of liposomal ceramide to a cell suspension.
Figure 27A:
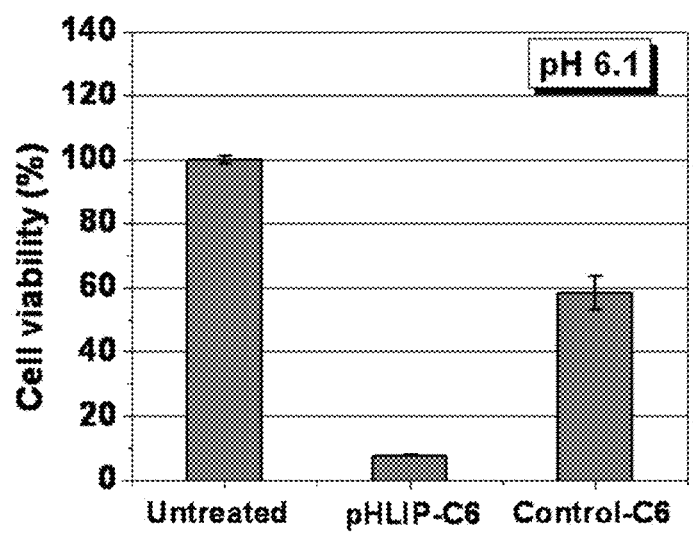
FIGS. 27A and 27B are a series of bar charts demonstrating the results of pHLIP-mediated delivery of liposomal ceramide to cell suspension. Delivery of ceramide (C6) using pHLIP-liposomes lead to a significantly greater amount of cell death at low pH compared to the level of cell death at high pH. Moreover, ceramide (C6) pHLIP-liposomes lead to a significantly greater amount of cell death at low pH compared to ceramide liposomes alone (in the absence of pHLIP) at low pH.
Figure 27B:
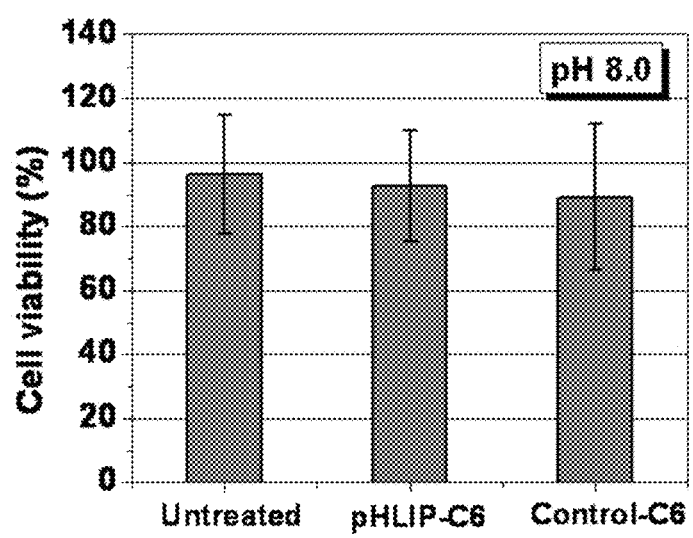

A schematic of pHLIP-mediated delivery of liposomal ceramide to cell suspension is provided in FIG. 26. FIGS. 27A and 27B are a series of bar charts demonstrating the results of pHLIP-mediated delivery of liposomal ceramide to cell suspension. Delivery of ceramide (C6) using pHLIP-liposomes led to a significantly greater amount of cell death at low pH compared to the level of cell death at high pH. Moreover, ceramide (C6) pHLIP-liposomes led to a significantly greater amount of cell death at low pH compared to ceramide liposomes alone (in the absence of pHLIP) at low pH.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A liposome comprising non-pore forming pHLIP polypeptide monomers covalently attached to polar headgroups of phospholipids in the lipid bilayer of said liposome, wherein the hydrophobic phospholipid tail region of the lipid bilayer of said liposome is substantially free of said pHLIP polypeptide monomers, wherein said liposome further comprises a hydrophobic or non-polar cargo incorporated into said lipid bilayer, and wherein said cargo comprises a therapeutic agent or a diagnostic agent.

2. The liposome of claim 1, wherein the pHLIP polypeptide monomers are directly attached to polar headgroups of phospholipids in the lipid bilayer.

3. The liposome of claim 1, wherein the cargo is non-polar.

4. The liposome of claim 1, wherein the cargo comprises a gene regulation agent.

5. The liposome of claim 1, wherein the cargo comprises a therapeutic agent.

6. The liposome of claim 5, wherein the therapeutic agent comprises a chemotherapeutic or anti-tumor compound.

7. The liposome of claim 6, wherein the chemotherapeutic compound comprises paclitaxel.

8. The liposome of claim 6, wherein the chemotherapeutic compound comprises ceramide.

9. The liposome of claim 6, wherein the chemotherapeutic compound comprises doxorubicin.

10. The liposome of claim 1, wherein the cargo comprises a diagnostic agent.

11. The liposome of claim 10, wherein the diagnostic agent comprises an imaging agent.

12. The liposome of claim 11, wherein the imaging agent comprises a fluorescent imaging agent.

13. The liposome of claim 12, wherein the fluorescent imaging agent comprises a fluorescent dye.

14. The liposome of claim 12, wherein the fluorescent imaging agent comprises rhodamine or fluorescein.

15. The liposome of claim 14, wherein the rhodamine forms part of a rhodamine-fatty acid.

16. The liposome of claim 1, wherein
(a) the amino-terminal ends of the pHLIP polypeptide monomers are covalently attached to the polar headgroups, or
(b) the carboxy-terminal ends of the pHLIP polypeptide monomers are covalently attached to the polar headgroups.

17. The liposome of claim 1, wherein the lipid bilayer comprises polyethylene glycol (PEG)-phospholipids.

18. The liposome of claim 1, wherein each of the pHLIP polypeptide monomers comprises 13 to 25 amino acids, and the 13 to 25 amino acids comprise at least 6 non-polar amino acids, and at least 1 protonatable amino acid.

19. A method of delivering a cargo into a target cell comprising contacting said target cell with cargo-loaded pHLIP$^+$ liposomes according to claim 1, wherein at least 10% more of said cargo is delivered to said target cell compared to the amount delivered using pHLIP$^-$ liposomes.

20. The method of claim 19, wherein said target cell is characterized by a microenvironment comprising a low pH.

21. The method of claim 20, wherein said target cell is a tumor cell, ischemic cell, inflamed cell, bacterially-infected cell, fungus-infected cells, or virally-infected cell.

22. A pharmaceutical composition comprising the liposome of claim 1.

23. A liposome comprising polymer-phospholipids in the lipid bilayer thereof, wherein non-pore forming pHLIP polypeptide monomers are covalently attached to the polymer-phospholipids, wherein the hydrophobic phospholipid tail region of the lipid bilayer of said liposome is substantially free of said pHLIP polypeptide monomers, wherein said liposome further comprises a hydrophobic or non-polar cargo incorporated into said lipid bilayer, and wherein said cargo comprises a therapeutic agent or a diagnostic agent.

24. The liposome of claim 23, wherein the polymer-phospholipids comprise polyethylene glycol (PEG)-phospholipids.

* * * * *

SEQUENCE LISTING

```
<160> NUMBER OF SEQ ID NOS: 52

<210> SEQ ID NO 1
<211> LENGTH: 34
<212> TYPE: PRT
<213> ORGANISM: Artificial Sequence
<220> FEATURE:
<223> OTHER INFORMATION: pHLIP variant

<400> SEQUENCE: 1

Gly Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly

<210> SEQ ID NO 2
<211> LENGTH: 40
<212> TYPE: PRT
<213> ORGANISM: Artificial Sequence
<220> FEATURE:
<223> OTHER INFORMATION: pHLIP variant

<400> SEQUENCE: 2

Ala Cys Glu Gln Asn Pro Ile Tyr Trp Ala Arg Tyr Trp Ala Arg Tyr
1               5                   10                  15

Ala Asp Trp Leu Phe Thr Thr Pro Leu Leu Leu Leu Asp Leu Ala Leu
            20                  25                  30

Leu Val Asp Ala Asp Glu Gly Thr
            35                  40

<210> SEQ ID NO 3
<211> LENGTH: 36
<212> TYPE: PRT
<213> ORGANISM: Artificial Sequence
<220> FEATURE:
<223> OTHER INFORMATION: pHLIP variant

<400> SEQUENCE: 3

Gly Gly Glu Gln Asn Pro Ile Tyr Trp Ala Arg Tyr Ala Asp Trp Leu
1               5                   10                  15
```

Phe Thr Thr Pro Leu Leu Leu Leu Asp Leu Ala Leu Leu Val Asp Ala
            20                  25                  30

Asp Glu Gly Thr
        35

<210> SEQ ID NO 4
<211> LENGTH: 35
<212> TYPE: PRT
<213> ORGANISM: Artificial Sequence
<220> FEATURE:
<223> OTHER INFORMATION: pHLIP variant

<400> SEQUENCE: 4

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Thr
        35

<210> SEQ ID NO 5
<211> LENGTH: 38
<212> TYPE: PRT
<213> ORGANISM: Artificial Sequence
<220> FEATURE:
<223> OTHER INFORMATION: pHLIP variant

<400> SEQUENCE: 5

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 6
<211> LENGTH: 38
<212> TYPE: PRT
<213> ORGANISM: Artificial Sequence
<220> FEATURE:
<223> OTHER INFORMATION: pHLIP variant

<400> SEQUENCE: 6

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 7
<211> LENGTH: 37
<212> TYPE: PRT
<213> ORGANISM: Artificial Sequence
<220> FEATURE:
<223> OTHER INFORMATION: pHLIP variant

<400> SEQUENCE: 7

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 8
<211> LENGTH: 36
<212> TYPE: PRT
<213> ORGANISM: Artificial Sequence
<220> FEATURE:
<223> OTHER INFORMATION: pHLIP variant

<400> SEQUENCE: 8

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 9
<211> LENGTH: 36
<212> TYPE: PRT
<213> ORGANISM: Artificial Sequence
<220> FEATURE:
<223> OTHER INFORMATION: pHLIP variant

<400> SEQUENCE: 9

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 10
<211> LENGTH: 39
<212> TYPE: PRT
<213> ORGANISM: Artificial Sequence
<220> FEATURE:
<223> OTHER INFORMATION: pHLIP variant

<400> SEQUENCE: 10

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 11
<211> LENGTH: 36
<212> TYPE: PRT
<213> ORGANISM: Artificial Sequence
<220> FEATURE:
<223> OTHER INFORMATION: pHLIP variant

<400> SEQUENCE: 11

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Cys Thr
        35

```
<210> SEQ ID NO 12
<211> LENGTH: 37
<212> TYPE: PRT
<213> ORGANISM: Artificial Sequence
<220> FEATURE:
<223> OTHER INFORMATION: pHLIP variant

<400> SEQUENCE: 12

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
                20                  25                  30

Asp Glu Gly Thr Gly
        35

<210> SEQ ID NO 13
<211> LENGTH: 37
<212> TYPE: PRT
<213> ORGANISM: Artificial Sequence
<220> FEATURE:
<223> OTHER INFORMATION: pHLIP variant

<400> SEQUENCE: 13

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
                20                  25                  30

Asp Glu Gly Thr Gly
        35

<210> SEQ ID NO 14
<211> LENGTH: 36
<212> TYPE: PRT
<213> ORGANISM: Artificial Sequence
<220> FEATURE:
<223> OTHER INFORMATION: pHLIP variant

<400> SEQUENCE: 14

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
                20                  25                  30

Asn Gln Gly Thr
        35

<210> SEQ ID NO 15
<211> LENGTH: 36
<212> TYPE: PRT
<213> ORGANISM: Artificial Sequence
<220> FEATURE:
<223> OTHER INFORMATION: pHLIP variant

<400> SEQUENCE: 15

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
                20                  25                  30

Asp Glu Gly Thr
        35

<210> SEQ ID NO 16
```

<211> LENGTH: 36
<212> TYPE: PRT
<213> ORGANISM: Artificial Sequence
<220> FEATURE:
<223> OTHER INFORMATION: pHLIP variant

<400> SEQUENCE: 16

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 17
<211> LENGTH: 36
<212> TYPE: PRT
<213> ORGANISM: Artificial Sequence
<220> FEATURE:
<223> OTHER INFORMATION: pHLIP variant

<400> SEQUENCE: 17

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
            20                  25                  30

Asp Glu Gly Thr
        35

<210> SEQ ID NO 18
<211> LENGTH: 36
<212> TYPE: PRT
<213> ORGANISM: Artificial Sequence
<220> FEATURE:
<223> OTHER INFORMATION: pHLIP variant

<400> SEQUENCE: 18

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr
        35

<210> SEQ ID NO 19
<211> LENGTH: 36
<212> TYPE: PRT
<213> ORGANISM: Artificial Sequence
<220> FEATURE:
<223> OTHER INFORMATION: pHLIP variant

<400> SEQUENCE: 19

Ala Ala Glu Gln Asn Pro Ile Tyr Trp Ala Arg Tyr Ala Glu Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 20
<211> LENGTH: 39
<212> TYPE: PRT
<213> ORGANISM: Artificial Sequence
<220> FEATURE:
<223> OTHER INFORMATION: pHLIP variant

<400> SEQUENCE: 20

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
            20                  25                  30

Val Asp Ala Asp Glu Gly Thr
            35

<210> SEQ ID NO 21
<211> LENGTH: 37
<212> TYPE: PRT
<213> ORGANISM: Artificial Sequence
<220> FEATURE:
<223> OTHER INFORMATION: pHLIP variant

<400> SEQUENCE: 21

Gly Glu Gln Asn Pro Ile Tyr Trp Ala Gln Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr Cys Gly
            35

<210> SEQ ID NO 22
<211> LENGTH: 38
<212> TYPE: PRT
<213> ORGANISM: Artificial Sequence
<220> FEATURE:
<223> OTHER INFORMATION: pHLIP variant

<400> SEQUENCE: 22

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly Thr Cys Gly
            35

<210> SEQ ID NO 23
<211> LENGTH: 38
<212> TYPE: PRT
<213> ORGANISM: Artificial Sequence
<220> FEATURE:
<223> OTHER INFORMATION: pHLIP variant

<400> SEQUENCE: 23

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
            35

<210> SEQ ID NO 24
<211> LENGTH: 38
<212> TYPE: PRT
<213> ORGANISM: Artificial Sequence
<220> FEATURE:
<223> OTHER INFORMATION: pHLIP variant

```
<400> SEQUENCE: 24

Gly Gly Glu Gln Asn Pro Ile Tyr Trp Ala Arg Tyr Asp Ala Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
            35

<210> SEQ ID NO 25
<211> LENGTH: 38
<212> TYPE: PRT
<213> ORGANISM: Artificial Sequence
<220> FEATURE:
<223> OTHER INFORMATION: pHLIP variant

<400> SEQUENCE: 25

Gly Gly Glu Gln Asn Pro Ile Tyr Trp Ala Arg Tyr Ala Trp Asp Leu
1               5                   10                  15

Phe Thr Thr Pro Leu Leu Leu Asp Leu Ala Leu Leu Val Asp Ala
            20                  25                  30

Asp Glu Gly Thr Cys Gly
            35

<210> SEQ ID NO 26
<211> LENGTH: 36
<212> TYPE: PRT
<213> ORGANISM: Artificial Sequence
<220> FEATURE:
<223> OTHER INFORMATION: pHLIP variant

<400> SEQUENCE: 26

Ala Ala Glu Gln Asn Pro Ile Tyr Trp Ala Arg Tyr Ala Asp Trp Leu
1               5                   10                  15

Phe Thr Thr Gly Leu Leu Leu Asp Leu Ala Leu Leu Val Asp Ala
            20                  25                  30

Asp Glu Gly Thr
            35

<210> SEQ ID NO 27
<211> LENGTH: 37
<212> TYPE: PRT
<213> ORGANISM: Artificial Sequence
<220> FEATURE:
<223> OTHER INFORMATION: pHLIP variant

<400> SEQUENCE: 27

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
            35

<210> SEQ ID NO 28
<211> LENGTH: 38
<212> TYPE: PRT
<213> ORGANISM: Artificial Sequence
<220> FEATURE:
<223> OTHER INFORMATION: pHLIP variant

<400> SEQUENCE: 28

Asp Asp Asp Glu Asp Asn Pro Ile Tyr Trp Ala Arg Tyr Ala His Trp
```

```
1               5                   10                  15
Leu Phe Thr Thr Pro Leu Leu Leu Leu His Gly Ala Leu Leu Val Asp
                20                  25                  30

Ala Asp Glu Gly Cys Thr
                35

<210> SEQ ID NO 29
<211> LENGTH: 37
<212> TYPE: PRT
<213> ORGANISM: Artificial Sequence
<220> FEATURE:
<223> OTHER INFORMATION: pHLIP variant

<400> SEQUENCE: 29

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
                20                  25                  30

Ala Asp Glu Cys Thr
                35

<210> SEQ ID NO 30
<211> LENGTH: 37
<212> TYPE: PRT
<213> ORGANISM: Artificial Sequence
<220> FEATURE:
<223> OTHER INFORMATION: pHLIP variant

<400> SEQUENCE: 30

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
                20                  25                  30

Ala Asn Glu Cys Thr
                35

<210> SEQ ID NO 31
<211> LENGTH: 34
<212> TYPE: PRT
<213> ORGANISM: Artificial Sequence
<220> FEATURE:
<223> OTHER INFORMATION: pHLIP variant

<400> SEQUENCE: 31

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
                20                  25                  30

Glu Thr

<210> SEQ ID NO 32
<211> LENGTH: 35
<212> TYPE: PRT
<213> ORGANISM: Artificial Sequence
<220> FEATURE:
<223> OTHER INFORMATION: pHLIP variant

<400> SEQUENCE: 32

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
                20                  25                  30
```

```
<210> SEQ ID NO 33
<211> LENGTH: 34
<212> TYPE: PRT
<213> ORGANISM: Artificial Sequence
<220> FEATURE:
<223> OTHER INFORMATION: pHLIP variant

<400> SEQUENCE: 33

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 34
<211> LENGTH: 32
<212> TYPE: PRT
<213> ORGANISM: Artificial Sequence
<220> FEATURE:
<223> OTHER INFORMATION: pHLIP variant

<400> SEQUENCE: 34

Ala Lys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: pHLIP variant

<400> SEQUENCE: 35

Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: pHLIP variant

<400> SEQUENCE: 36

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Cys Gly
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: pHLIP variant

<400> SEQUENCE: 37
```

Glu Gly Thr
      35

```
Ala Glu Asp Gln Asn Pro Tyr Trp Ala Arg Tyr Ala Asp Trp Leu Phe
1               5                   10                  15

Thr Thr Pro Leu Leu Leu Glu Leu Ala Leu Leu Val Glu Cys Gly
            20                  25                  30
```

<210> SEQ ID NO 38
<211> LENGTH: 30
<212> TYPE: PRT
<213> ORGANISM: Artificial Sequence
<220> FEATURE:
<223> OTHER INFORMATION: pHLIP variant

<400> SEQUENCE: 38

```
Ala Lys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30
```

<210> SEQ ID NO 39
<211> LENGTH: 30
<212> TYPE: PRT
<213> ORGANISM: Artificial Sequence
<220> FEATURE:
<223> OTHER INFORMATION: pHLIP variant

<400> SEQUENCE: 39

```
Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30
```

<210> SEQ ID NO 40
<211> LENGTH: 32
<212> TYPE: PRT
<213> ORGANISM: Artificial Sequence
<220> FEATURE:
<223> OTHER INFORMATION: pHLIP variant

<400> SEQUENCE: 40

```
Ala Lys Glu Asp Gln Asn Asp Pro Tyr Trp Ala Arg Tyr Ala Asp Trp
1               5                   10                  15

Leu Phe Thr Thr Pro Leu Leu Leu Asp Leu Ala Leu Leu Val Gly
            20                  25                  30
```

<210> SEQ ID NO 41
<211> LENGTH: 34
<212> TYPE: PRT
<213> ORGANISM: Artificial Sequence
<220> FEATURE:
<223> OTHER INFORMATION: pHLIP variant

<400> SEQUENCE: 41

```
Thr Glu Asp Ala Asp Val Leu Leu Ala Leu Asp Leu Leu Leu Leu Pro
1               5                   10                  15

Thr Thr Phe Leu Trp Asp Ala Tyr Arg Ala Trp Tyr Pro Asn Gln Glu
            20                  25                  30

Cys Ala
```

<210> SEQ ID NO 42
<211> LENGTH: 20
<212> TYPE: PRT
<213> ORGANISM: Artificial Sequence
<220> FEATURE:

<223> OTHER INFORMATION: pHLIP variant

<400> SEQUENCE: 42

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 43
<211> LENGTH: 21
<212> TYPE: PRT
<213> ORGANISM: Artificial Sequence
<220> FEATURE:
<223> OTHER INFORMATION: pHLIP variant

<400> SEQUENCE: 43

Ala Glu Gln Asn Pro Ile Tyr Trp Ala Arg Tyr Ala Asp Trp Leu Phe
1               5                   10                  15

Thr Thr Pro Cys Leu
            20

<210> SEQ ID NO 44
<211> LENGTH: 21
<212> TYPE: PRT
<213> ORGANISM: Artificial Sequence
<220> FEATURE:
<223> OTHER INFORMATION: pHLIP variant

<400> SEQUENCE: 44

Ala Cys Glu Gln Asn Pro Ile Tyr Trp Ala Arg Tyr Ala Asp Trp Leu
1               5                   10                  15

Phe Thr Thr Pro Leu
            20

<210> SEQ ID NO 45
<211> LENGTH: 20
<212> TYPE: PRT
<213> ORGANISM: Artificial Sequence
<220> FEATURE:
<223> OTHER INFORMATION: pHLIP variant

<400> SEQUENCE: 45

Ala Glu Gln Asn Pro Ile Tyr Phe Ala Arg Tyr Ala Asp Trp Leu Phe
1               5                   10                  15

Thr Thr Pro Leu
            20

<210> SEQ ID NO 46
<211> LENGTH: 21
<212> TYPE: PRT
<213> ORGANISM: Artificial Sequence
<220> FEATURE:
<223> OTHER INFORMATION: pHLIP variant

<400> SEQUENCE: 46

Lys Glu Asp Gln Asn Pro Trp Ala Arg Tyr Ala Asp Leu Leu Phe Pro
1               5                   10                  15

Thr Thr Leu Ala Trp
            20

<210> SEQ ID NO 47
<211> LENGTH: 22
<212> TYPE: PRT
<213> ORGANISM: Artificial Sequence
<220> FEATURE:
<223> OTHER INFORMATION: pHLIP variant

<400> SEQUENCE: 47

Ala Cys Glu Asp Gln Asn Pro Trp Ala Arg Tyr Ala Asp Leu Leu Phe
1               5                   10                  15
Pro Thr Thr Leu Ala Trp
            20

<210> SEQ ID NO 48
<211> LENGTH: 24
<212> TYPE: PRT
<213> ORGANISM: Artificial Sequence
<220> FEATURE:
<223> OTHER INFORMATION: pHLIP variant

<400> SEQUENCE: 48

Ala Cys Glu Asp Gln Asn Pro Trp Ala Arg Tyr Ala Asp Trp Leu Phe
1               5                   10                  15
Pro Thr Thr Leu Leu Leu Leu Asp
            20

<210> SEQ ID NO 49
<211> LENGTH: 22
<212> TYPE: PRT
<213> ORGANISM: Artificial Sequence
<220> FEATURE:
<223> OTHER INFORMATION: pHLIP variant

<400> SEQUENCE: 49

Ala Cys Glu Glu Gln Asn Pro Trp Ala Arg Tyr Ala Glu Leu Leu Phe
1               5                   10                  15
Pro Thr Thr Leu Ala Trp
            20

<210> SEQ ID NO 50
<211> LENGTH: 24
<212> TYPE: PRT
<213> ORGANISM: Artificial Sequence
<220> FEATURE:
<223> OTHER INFORMATION: pHLIP variant

<400> SEQUENCE: 50

Ala Cys Glu Glu Gln Asn Pro Trp Ala Arg Tyr Ala Glu Trp Leu Phe
1               5                   10                  15
Pro Thr Thr Leu Leu Leu Leu Glu
            20

<210> SEQ ID NO 51
<211> LENGTH: 25
<212> TYPE: PRT
<213> ORGANISM: Artificial Sequence
<220> FEATURE:
<223> OTHER INFORMATION: pHLIP variant

<400> SEQUENCE: 51

Ala Cys Glu Glu Gln Asn Pro Trp Ala Arg Tyr Leu Glu Trp Leu Phe
1               5                   10                  15
Pro Thr Glu Thr Leu Leu Leu Glu Leu
            20                  25

<210> SEQ ID NO 52
<211> LENGTH: 36
<212> TYPE: PRT

```
<213> ORGANISM: Artificial Sequence
<220> FEATURE:
<223> OTHER INFORMATION: pHLIP variant

<400> SEQUENCE: 52

Ala Gln Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
            35
```